(12) United States Patent
Löwenhielm et al.

(10) Patent No.: US 11,376,345 B2
(45) Date of Patent: Jul. 5, 2022

(54) HYDROGEL COMPOSITION AND ITS USES

(71) Applicants: Peter Löwenhielm, Täby (SE); Michael Malkoch, Täby (SE); Oliver Andrén, Stockholm (SE)

(72) Inventors: Peter Löwenhielm, Täby (SE); Michael Malkoch, Täby (SE); Oliver Andrén, Stockholm (SE)

(73) Assignee: SENTIGEL AB, Taby (SE)

( * ) Notice: Subject to any disclaimer, the term of this patent is extended or adjusted under 35 U.S.C. 154(b) by 268 days.

(21) Appl. No.: 16/765,344

(22) PCT Filed: Nov. 23, 2018

(86) PCT No.: PCT/EP2018/082385
§ 371 (c)(1),
(2) Date: May 19, 2020

(87) PCT Pub. No.: WO2019/101929
PCT Pub. Date: May 31, 2019

(65) Prior Publication Data
US 2021/0213160 A1    Jul. 15, 2021

(30) Foreign Application Priority Data

Nov. 23, 2017    (SE) .................................. 1751442-3

(51) Int. Cl.
*A61L 26/00* (2006.01)
*A61L 27/34* (2006.01)
*A61L 27/52* (2006.01)
*A61L 27/54* (2006.01)

(52) U.S. Cl.
CPC ......... *A61L 26/0066* (2013.01); *A61L 26/008* (2013.01); *A61L 26/0019* (2013.01); *A61L 27/34* (2013.01); *A61L 27/52* (2013.01); *A61L 27/54* (2013.01); *A61L 2300/404* (2013.01); *A61L 2420/02* (2013.01)

(58) Field of Classification Search
None
See application file for complete search history.

(56) References Cited

FOREIGN PATENT DOCUMENTS

| WO | WO 03/072155 A1 | 9/2003 |
| WO | WO 2007/082061 A2 | 7/2007 |
| WO | WO 2015/002888 A1 | 1/2015 |

OTHER PUBLICATIONS

Andren et al., "Multifunctional Poly(ethylene glycol): Synthesis, Characterization, and Potential Applications of Dendritic-Linear-Dendritic Block Copolymer Hybrids", Macromolecules, 2013, 46: 3726-3736.
Duran-Lara et al., "Investigation of Lysine-Functionalized Dendrimers as Dichlorvos Detoxification Agents", Biomacromolecules, 2015, 16: 3434-3444.
Ghobril et al., "A Dendritic Thioester Hydrogel Based on Thiol-Thioester Exchange as a Dissolvable Sealant System for Wound Closure", Angewandte Communications Int. Ed., 2013, 52: 14070-14074.
Lancelot et al., "DNA Transfection to Mesenchymal Stem Cells Using a Novel Type of Pseudodendrimer Based on 2,2-Bis(hydroxymethyl)propionic Acid", Bioconjugate Chemistry, 2017, 28: 1135-1150.
Lin et al., "Injectable supramolecular hydrogel formed from α-cyclodextrin and PEGylated arginine-functionalized poly (L-lysine) dendron for sustained MMP-9 shRNA plasmid delivery", Acta Biomaterialia, 2017, 49: 456-471.
Movellan et al., "Amphiphilic dendritic derivatives as nanocarriers for the targeted delivery of antimalarial drugs", Biomaterials, , 2014, 35: 7940-7950.
Navath et al., "Amino Acid-Functionalized Dendrimers with Heterobifunctional Chemoselective Peripheral Groups for Drug Delivery Applications", Biomacromolecules, 2010, 11: 1544-1563.
Navath et al., "Injectable PAMAM DendrimerPEG Hydrogels for the Treatment of Genital Infections: Formulation and in Vitro and in Vivo Evaluation", Molecular Pharmaceutics, 2011, 8: 1209-1223.
Press release "New amine functional products" from Polymer Factory Sweden AB dated Oct. 5, 2017 [retrieved on Apr. 16, 2018] retrieved from the internet: <http://www.polymerfactory.com/news/press-releases/new-amine-functional-products/>.
Attachment to press release "Aminofunctional Hyperranched Polyesters" [retrieved on Apr. 16, 2018] retrieved from the Internet: <http://www.polymerfactory.com/wp-content/uploads/2017/10/Amine-functional-HBPs-FINAL.pdf>.
Stenstrom et al., "Synthesis and in Vitro Evaluation of Monodisperse Amino-Functional Polyester Dendrimers with Rapid Degradability and Antibacterial Properties", Biomacromolecules, 2017, 18: 4323-4330.
Villa-Camacho et al., "The efficacy of a lysine-based dendritic hydrogel does not differ from those of commercially available tissue sealants and adhesives: an ex vivo study", BMC Musculoskeletal Disorders, 2015, 16:116.

*Primary Examiner* — Hasan S Ahmed
*Assistant Examiner* — Randeep Singh
(74) *Attorney, Agent, or Firm* — James S. Keddie; Bozicevic, Field & Francis LLP

(57) ABSTRACT

The present invention relates to an antibacterial co-polymer comprising a water soluble backbone polymer having in at least one end a dendritic or hyperbranched polymer of generation 1 to 6 wherein at least one functional group comprising a carboxylic amine has been covalently attached to the periphery of the dendritic or hyperbranched polymer. The present invention also relates to said anti-bacterial co-polymer when said co-polymer has been cross-linked with a cross-linking agent and to uses of the cross-linked co-polymer in a hydrogel for the treatment or prevention of bacterial infections, particularly in surgical site infections (SSIs).

13 Claims, 8 Drawing Sheets

C)

HYDROGEL COMPOSITION AND ITS USES

CROSS-REFERENCE TO RELATED APPLICATIONS

This application is a § 371 national phase of International Application No. PCT/EP2018/082385, filed on Nov. 23, 2018, which claims the benefit of Swedish Patent Application No. 1751442-3, filed on Nov. 23, 2017, which applications are incorporated by reference herein.

FIELD OF THE INVENTION

The present invention relates to the field of polymers possessing antimicrobial properties, and particularly to hydrogels comprising said antimicrobial polymers. More particularly, the invention relates to the field of cross-linked polymer based hydrogels possessing antimicrobial properties for use in medical applications such as in the treatment or prevention of surgical site infections.

BACKGROUND OF THE INVENTION

Polymers and Dendritic Structures

Polymers are exceedingly versatile materials that can be insulating or conducting, ductile or brittle, thermally insulating and corrosion resistant to name a few. Polymers are constructed by covalently linking many small molecules, called monomers, into long chains. The monomers can be assembled into a vast array of compositions and more importantly configurations. Since the basic component of a polymer is one or several monomers connected into a longer chain, this chain can have as many compositions as there are monomers in the chain. If the monomer across the entire chain is the same it is called a homopolymer and if two or several monomers are used it is called a co-polymer. The monomers can also be assembled into one single long chain or be divided into shorter chains connected together, called branching.

Dendrimers are among the latest addition to the polymer family. They are branched precision structures with a perfection exceeding commercial peptide and proteins. Their defined structure along with high degree of functionality allows in depth structure to property evaluation highly suitable for biomedical research. Just like polymers dendrimers can be constructed in an array of different architectures, generally they can be divided into the monodisperse and polydisperse frameworks.

The dendritic family also comprises hyperbranched polymers, dendronized polymers as well as linear-dendritic-co-polymers (LD). Hyperbranched polymers are structurally imperfect dendritic structures with a set of properties that is reasonably similar to that of the corresponding dendrimers. The concept pseudogeneration is used to characterize hyperbranched structures, where a hyperbranched polymer of pseudogeneration two theoretical has the same number of end groups and molecular weight as a dendrimer of generation two. In comparison to dendrimers and dendrons, hyperbranched polymers can be synthesized in large scale through one-pot procedures, which enables commercial availability and promotes the use of hyperbranched polymers in application-driven research.

Dendrimers that can carry more than one type of functionality belong to the more challenging dendritic structures to construct. Nevertheless, since their potential is envisioned to be found in more demanding fields, e.g. nanomedicine, dendrimer chemists are now challenged to accomplish the synthesis of these structures efficiently. The final architecture expresses at least two different functional groups, which can be located either on the surface of the dendrimer or on the inside. These scaffolds can further be functionalized with different substituents depending on the targeted application.

Dendritic architectures based on the monomer 2, 2-bis-methylolpropionic acid (bis-MPA) have previously been disclosed as being of particular use in application driven research. The bis-MPA molecule has successfully been explored for the construction of a large number of dendritic materials, such as from monodisperse dendrons and dendrimers to polydisperse hyperbranched polymers and dendritic-linear hybrids. (*Dendritic architectures based on bis-MPA: functional polymeric scaffolds for application driven research*, Chem. Soc. Rev., 2013, 42, 5858-5879).

Antimicrobial Peptides

Antimicrobial peptides (AMPs) are part of organisms natural defense against bacteria and rely on the negatively charged nature of bacterial cell walls by disrupting the membrane or inserting to target internal components. Resistance has been observed for AMPs but is much less widespread as compared to conventional antibiotics. The AMP previously found in literature often have a few things in common; I: they have a cationic charge often in the form of a primary amine. II: They are slightly amphiphilic in nature containing hydrophilic and hydrophobic segments.

One application where the use of antibiotics is critical is in conjunction with a surgical intervention. During a surgical intervention antibiotic prophylaxis is required to protect the surgical site from bacterial infections. Despite all precautions, between 2-5% of all surgical interventions result in surgical site infections (SSIs). A post-operative infection can lead to unnecessary pain and suffering and even be potentially life threatening. Overall, the mortality rate associated with SSIs is estimated at 5% and SSIs have been identified to increase the cost associated with surgical intervention by approximately one third. Even a seemingly minor infection may give rise to discomfort and increased burden on the health care system. However, treatment protocols relying on regular antibiotics result in the emergence of resistant or multiresistant bacterial strains impossible to treat. Therefore, there is a need to decrease the risk of complications due to post-operative infections.

Antimicrobial hydrogels based on dimethyldecylammonium chitosan (with high quaternization)-graft-poly(ethylene glycol) methacrylate (DMDC-Q-g-EM) and poly(ethylene glycol) diacrylate were shown to have antimicrobial efficacy against *Pseudomonas aeruginosa*, *Escherichia coli*, *Staphylococcus aureus* and *Fusarium solani*. The proposed mechanism of the antimicrobial activity of the polycationic hydrogel is by attraction of sections of anionic microbial membrane into the internal nanopores of the hydrogel, like an 'anion sponge', leading to microbial membrane disruption and then microbe death. The hydrogel was applied as a coating and cured by ultraviolet irradiation. An animal study showed that the hydrogels prepared by the described method were biocompatible with rabbit conjunctiva and displayed no toxicity to the epithelial cells or the underlying stroma. (P. Li, Y. F. Poon, W. F. Li, H. Y. Zhu, S. H. Yeap, Y. Cao, X. B. Qi, C. C. Zhou, M. Lamrani, R. W. Beuerman, E. T. Kang, Y. G. Mu, C. M. Li, M. W. Chang, S. S. J. Leong, M. B. Chan-Park, Nat Mater 2011, 10, 149).

US2016287745A1 relates to dissolvable hydrogel compositions and methods of uses, e.g., but not limited to, in wound management. The document discloses a selection process for monomers and generations of dendrimers to achieve desired properties in the end product. More specifically, Polyethylene Glycol (PEG)-based multi-aminated dendrimers and PEG cross-linkers with N-hydroxysuccinimide esters (NHS) moieties are disclosed therein. Similar polymers comprising a PEG cross-linker are discussed in US2014349922A1.

U.S. Pat. No. 8,410,189B discloses a surgical "glue" including a dendrimer generation 5 (G5) injectable hydrogel for cataract gap filling. It also describes a dendrimer generation 8 (G8) sealant/hydrogel designed to degrade over time with new tissue regrowth. An excess of free primary amines in the cured hydrogel gives antimicrobial properties.

There is still a need to identify improved or at least alternative means for obviating the problems associated with bacterial infections that may arise in open wounds or tissue areas, such as during a surgical intervention. There is also an ongoing need in society to further decrease the usage of traditional antibiotics for the purpose of avoiding the increase in general antibiotic resistance in bacteria.

SUMMARY OF THE INVENTION

The above needs have now been attended to, or at least mitigated by the provision herein of a co-polymer comprising a water soluble backbone polymer having in at least one end a dendritic or hyperbranched polymer, wherein said dendritic or hyperbranched polymer are of generation 1 to 6 (G1 to G6) and wherein at least one functional group comprising a carboxylic amine is covalently attached to the periphery of the dendritic or hyperbranched polymer, and to its various uses in methods and compositions presented herein, particularly in the context of SSI (Surgical Site Interventions) and when in the form of a hydrogel as described further herein.

In a preferred aspect, said water soluble backbone polymer is a water soluble linear backbone polymer. More specifically, there is provided herein a co-polymer comprising a water soluble backbone polymer having in at least one end a dendritic or hyperbranched polymer, wherein said dendritic or hyperbranched polymer is of generation 1 to 6 (G1 to G6) and wherein at least one functional group comprising a carboxylic amine is covalently attached to the periphery of the dendritic or hyperbranched polymer, for use as a medicament.

There is also provided herein a composition comprising said co-polymer and a cross-linking agent (cross-linked polymer) as further explained herein, as well as uses of said co-polymer and said composition in a method of medical treatment, such as in the treatment or prevention of a bacterial infection. The composition is most preferably presented in the form of a hydrogel comprising said cross-linked co-polymer, which hydrogel is used herein to apply a protective coating to a tissue or a wound surface or to a medical device to prevent or treat, such as by preventing growth and/or colonization of a bacterial infection at such as location. The composition may form part of, or be coated onto, a wound dressing or the like, to be applied or attached onto a body surface, such as a tissue or a wound surface.

There is further herein presented a hydrogel comprising said cross-linked co-polymer that is able to provide dual advantages in the form of an antimicrobial effect and a physical effect in the form of a barrier to prevent the spread and/or growth of bacteria at a site likely to be exposed to bacteria. A further advantage of the cross-linked co-polymer of the hydrogel is that it is biodegradable and rapidly broken down into non-toxic components in the body after use. As mentioned herein, these advantages are particularly useful in a surgical setting.

When used in the context of a hydrogel, it is important that the co-polymer and the cross-linking agent are kept separate until just before use, as will be further described herein.

Furthermore, there is also provided a kit of parts comprising: a) a dispenser comprising a co-polymer or a composition comprising a co-polymer as disclosed herein and b) a dispenser comprising a cross-linking agent.

The present disclosure also relates to a use of the composition comprising a co-polymer and a cross-linking agent for the treatment or pre-treatment of a surface of a medical implant, by applying said composition to at least a part of a surface of said medical implant.

Various other objects and advantages of the present invention will become apparent from the drawings and the following detailed description of the invention.

BRIEF DESCRIPTION OF THE FIGURES

The following detailed description will be more fully understood in view of the figures, in which.

DETAILED DESCRIPTION

Definitions

Herein, it is often referred to "generations" of dendrimer or hyperbranched polymer structures. A generation may be referred to as "G1" for generation 1 and "G2" for generation 2, and so forth. Herein, polymer structures up to the sixth (G6) dendritic or hyperbranched generation have been prepared, but higher generations are also envisaged and encompassed by the present disclosure. A generation of a dendrimer refers to the number of repeated branching cycles that are performed during its synthesis, starting from a core (divergent approach) or building from the outside to in (convergent approach). There is also a third synthetic pathway leading to a hyperbranched dendrimer structure. In general, e.g. if the branching reactions are performed four times, the resulting dendrimer can be referred to as a fourth generation dendrimer. It is estimated that each successive generation results in a dendrimer about twice the molecular weight of the previous generation. The higher the generation, the more functional groups are exposed on the surface of the dendrimer which provides for adaptation of the dendrimer functionality for the intended use. Herein, polymer structures having a water soluble (linear) backbone polymer are disclosed, wherein the (linear) polymer backbone structure in one or two peripheral ends thereof comprises a dendritic or hyperbranched polymer scaffold, of any of the generations presented herein.

When a degree of branching is referred to herein in relation to a hyperbranched scaffold structure, this is defined as the ratio between perfect branches and the sum of all branches in the branched section of the co-polymer. The degree of branching was calculated using the Fréchet equation. According to previous work performed by Magnusson et al. the quaternary bis-MPA carbon has a chemical shift δ (ppm ((100)MHz, DMSO-D6)) of 50.1 for terminal (T), 49.4 for unreacted bis-MPA, 48.2 for linear (L), 47.5 for linear-acid, 46.2 for dendritic (D). Using the integrals of the signals characteristic to the specific monomer units, the degree of branching (DB) was calculated from Formula 2.

$$DB = \frac{D+T}{D+T+L} \quad \text{(Formula 2)}$$

Figure 1:
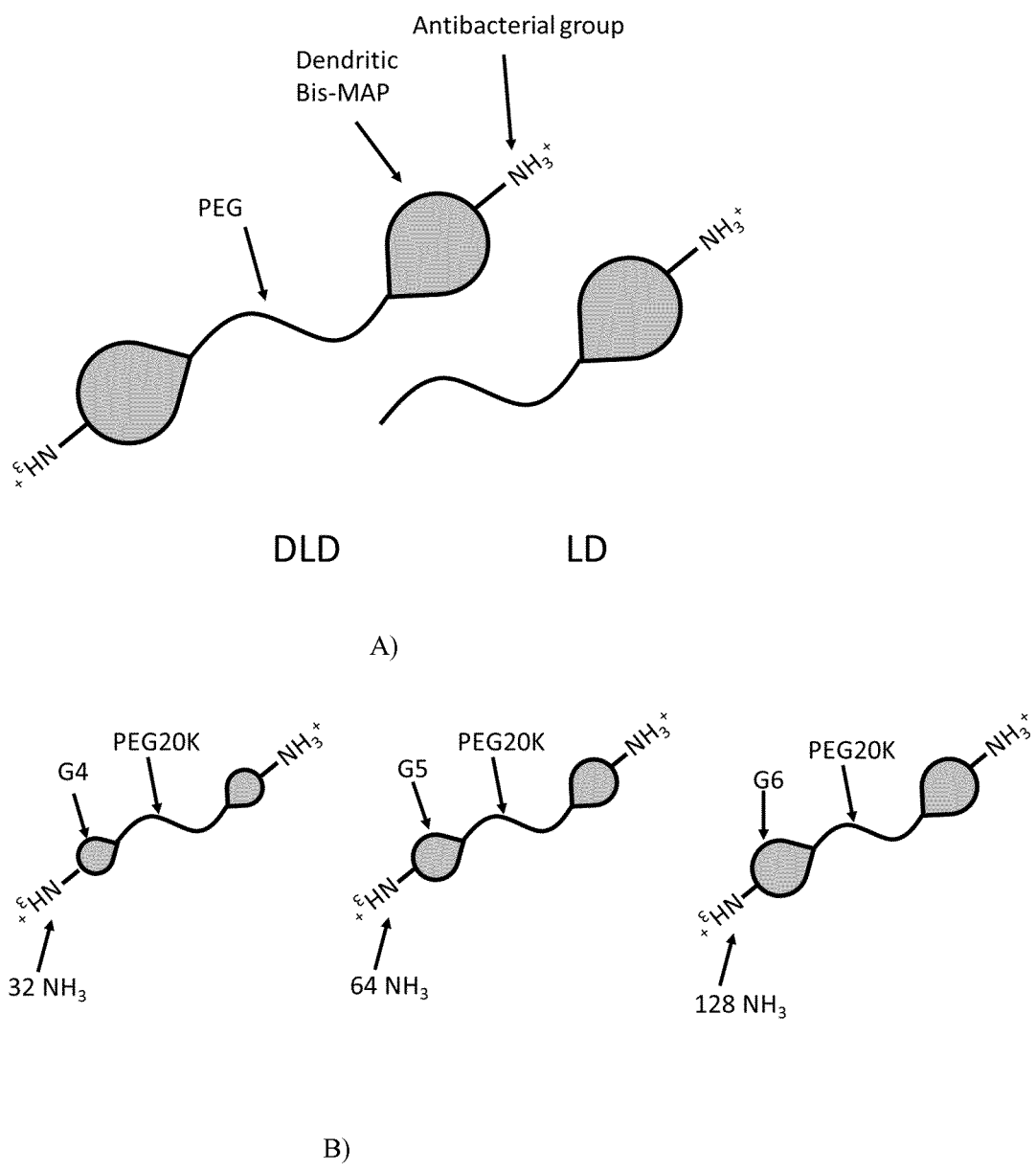
FIG. 1a is a linear backbone polymer according to the present disclosure having in each end bis-MPA dendritic polymers (scaffolds) to which antibacterial functional groups are covalently attached.
FIG. 1b shows dendrimers of generation 4, 5 and 6 respectively also indicating the number of cations in the periphery of the dendrimer or hyper branched scaffold depending of dendrimer generation.
FIG. 1c) is an schematic illustration of a plausible molecular structure of the hydrogel.
Figure 1:
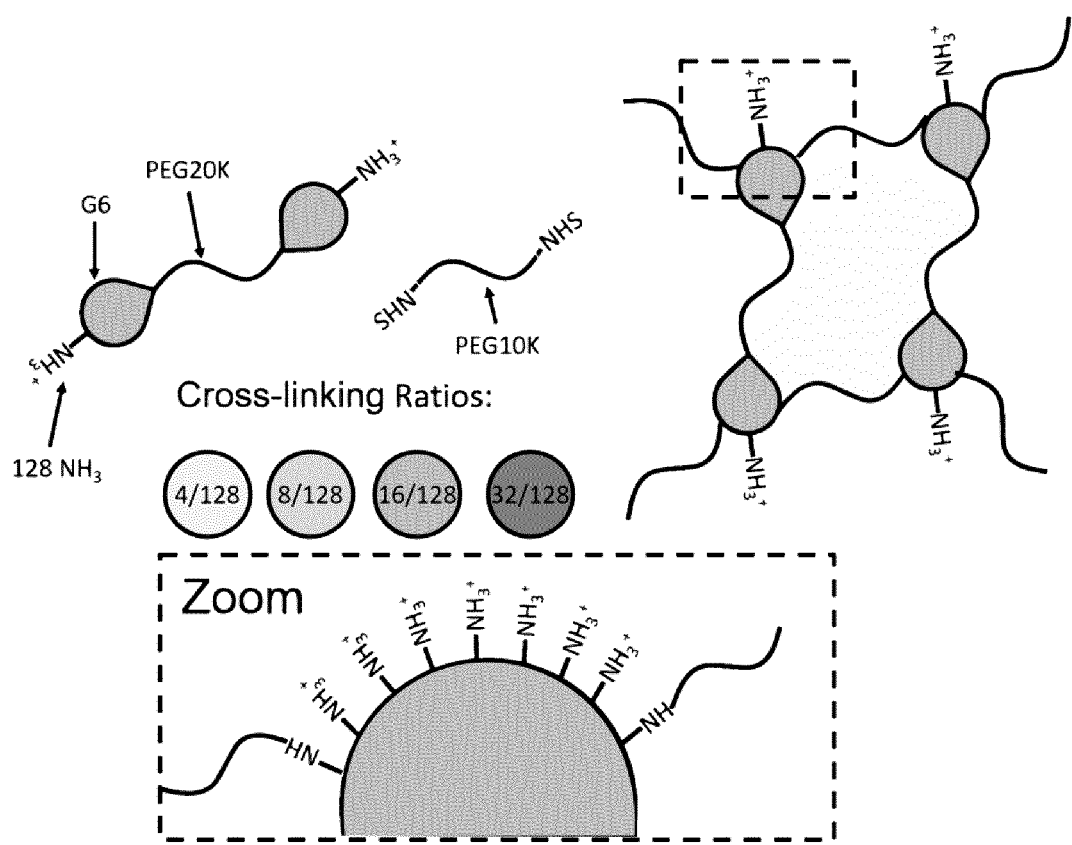

Perfect dendritic structure DB=1
Hyperbranched <1
Nomenclature of Polymers
Materials discussed herein may be named according to the following scheme:
A co-polymer with one linear and one dendritic block is named Linear-dendritic co-polymer (LD) (FIG. 1a):
[functional group]-[linear polymer] [molecular weight of linear polymer]-[Dendritic generation] [hb]*-([Peripheral functional group])
A co-polymer with a linear block and dendritic block at each end is named Dendritic linear dendritic co-polymer (DLD) (FIG. 1a).
[linear polymer] [molecular weight of linear polymer]-[Dendritic generation] [hb]*-([Peripheral functional group])
* only if DB<1
Peripheral functional group $NH_3^+$ refers to any amine such as β-Alanin.
Peripheral functionality may also define the number of amines in the periphery of the dendritic or hyperbranched structure which number may be dependent on the dendritic generation of the polymer (e.g. 32, 64, and 128 amines for generation 4, 5, and 6, respectively). Examples of DLD materials presented herein include, but are not limited to PEG20k-G4-$(NH_3^+)_{32}$, PEG20k-G5-$(NH_3^+)_{64}$, PEG20k-G6-$(NH_3^+)_{128}$, PEG10k-G4-$(NH_3^+)_{32}$, PEG10k-G5-$(NH_3^+)_{64}$ and PEG10k-G6-$(NH_3^+)_{128}$. $NH_3^+$ (amine) functionality may be provided by the amino acid β-alanin. An example of an LD is Methyl-PEG10k-G6-$(NH_3^+)_{128}$.

A hydrogel comprises hydrophilic polymer networks ("cross-linked polymers") which renders the gels capable of holding large amounts of water in their three-dimensional networks. This property arises from the presence of physical and/or chemical cross-links that prevent dissolution of the polymer networks in an aqueous fluid.

A "cross-linked polymer" is a polymer in which covalent bonds connect different chains of polymers. Herein a "cross-linked polymer" is generally referred to as the polymer structure comprised and formed in the composition or the hydrogel upon the addition of a "cross-linking agent" to a co-polymer as described herein. A "cross-linked polymer" may hence herein comprise a LD- or a DLD material as described herein cross-linked with a cross-linking agent.

DETAILED DESCRIPTION

An object of the present invention is to minimize the risk of a surgical site infection (SSI), through applying a protective antibacterial coating in the form of a composition, more particularly an antibacterial hydrogel comprising a co-polymer and a cross-linking agent as disclosed herein, at the site of intervention, e.g. at a tissue or a wound surface. Another object is to treat or pre-treat a medical device with said hydrogel before said medical device is to be introduced into the human or animal body. This can be done to avoid a bacterial infection developing in association with the introduction of said medical device into the body.

The polymer material in the form of a Linear Dendritic (LD)-co-polymer or Dendritic Linear Dendritic (DLD)-co-polymer material, i.e. a two-armed co-polymer (DLD) as further defined herein, or a three-armed or four-armed variant of said co-polymer as described elsewhere herein, or hyperbranched variants thereof, with both the solubility benefits of a linear material as well as the multiple representations of peripheral functionality was proven herein to be very useful in the context of the present disclosure. As shown herein, the co-polymer may also in itself provide a use as a medicament, more specifically for the treatment or prevention of a bacterial infection, such as by inhibiting the growth and/or colonization of the bacteria on a surface as described herein.

The hydrogel serves the purpose of both providing a broad spectrum antibacterial effect and at the same time ensuring fixation in the intended area until the critical infection risk has passed. The hydrogel coating may be applied through a simple two component dispenser (spray) instantly solidifying under biological conditions. The antibacterial cross-linked co-polymer forming part of the hydrogel was designed to be biocompatible, biodegradable, have a broad spectrum mode of action and be effective towards resistant as well as multi-resistant bacterial strains.

Accordingly, there is provided herein a co-polymer, also including a hyperbranched polymer, said co-polymer comprising a water soluble backbone polymer having in at least one end a dendritic or hyperbranched polymer, wherein said dendritic or hyperbranched polymer are of generation 1 to 6

(G1 to G6) and wherein at least one functional group comprising a carboxylic amine is covalently attached to the periphery of the dendritic or hyperbranched polymer (scaffold). In particular, there is provided herein such a co-polymer for use as a medicament. The periphery of the dendritic or hyperbranched polymer may also be referred to herein as the outermost generation of the dendritic or hyperbranched polymer. The dendritic or hyperbranched polymer may also be referred to herein as the dendritic or hyperbranched polymer scaffold. Herein, the water soluble backbone polymer may be a water soluble linear backbone polymer.

Amines are formally derivatives of ammonia, wherein one or more hydrogen atoms have been replaced by substituents. The functionality of the periphery of a dendrimer or hyperbranched presented herein comprises a functional group comprising a carboxylic amine. Examples of carboxylic acid amines for use in the context of the present disclosure comprise but are not limited to any natural (or unnatural) amino acid(s) (i.e. a single amino acid providing carboxylic amine functionality) as well as oligomers comprising more than one amino acid, which may be the same or different as well as other organic molecules containing a carboxylic acid and a cationic entity.

There is also provided herein a polymer comprising a water soluble backbone polymer having in at least one end a hyperbranched polymer having a certain degree of branching (DB), more particularly a DB greater than zero and less than or equal to one (0<degree of branching≤1).

There is also provided a polymer wherein both ends of said water soluble backbone polymer comprises a dendritic or hyperbranched polymer as previously defined herein having at least one functional group comprising a carboxylic amine covalently attached to the periphery of the dendritic or hyperbranched polymer. This may in addition to a two-armed co-polymer also be referred to herein as a telechelic or di-end-functional polymer. A telechelic polymer or oligomer is a prepolymer capable of entering into further polymerization or other reactions through its reactive end-groups.

Herein, said dendritic or hyperbranched polymer may comprise the monomer 2, 2-Bis(hydroxymethyl)propionic acid (bis-MPA), or a closely related variant or analogue thereof providing the same function. Said bis-MPA molecule may also be modified in a suitable manner. Said water soluble backbone co-polymer may comprise polyethylene glycol (PEG), or a closely related variant or analogue thereof providing the same function. Said water soluble backbone co-polymer may also be a polyethylene glycol (PEG) or a co-polymer comprising polyethylene glycol (PEG). A water soluble backbone PEG molecule, such as a water soluble linear backbone PEG molecule, may have a molecular weight within the range of about 0.2 kDa to 200 kDa, such as within the range of 1 kDa to 150 kDa, 1 kDa to 100 kDa, 2 kDa to 75 kDa, 5 kDa to 50 kDa, 10 kDa to 50 kDa, 20 kDa to 50 kDa, 20 kDa to 30 kDa, or preferably 5 kDa to 40 kDa, or more preferably 10 kDa to 20 kDa, or about 2 kDa to 20 kDa, but is not limited thereto. More particularly, said PEG may have a molecular weight of about 1 kDa, 2 kDa, 3 kDa, 4 kDa, 5 kDa, 10 kDa, 20 kDa, 30 kD, 40 kDa, 50 kDa, 60 kDa, 70 kDa, 80 kDa, 90 kDa or 100 kDa. Herein, when e.g. "PEG20K" is referred to this means a PEG molecule of 20 kDa.

Modifications to a PEG backbone molecule are also envisaged herein, such as modifications in the form of co-polymerization with other monomers and/or PEG molecules comprising combinations in form of connections of shorter PEG segments by cleavable linkages such as esters, amides, carbonates, hydrazine, or disulfides. In addition to PEG, other variants of backbones are also envisaged, such as poly(lactic acid) or poly(caprolacton) or other biocompatible polymers with reactive end-groups. Further examples are polymers containing the monomers of valerolactide, lactide (d,d- or l, l-, meso or racemic mixture), trimethylene carbonate, caprolactone, paradioxanone, β-butyrolactone and 1,5-dioxepan-2-one or co-polymers thereof.

Particularly, said co-polymer may comprise a water soluble backbone polymer, such as a water soluble linear backbone polymer, comprising or that is polyethylene glycol (PEG), and a dendritic or hyperbranched polymer of the monomer 2, 2-Bis(hydroxymethyl)propionic acid (bis-MPA) comprising at least one functional group comprising a carboxylic amine covalently attached to the periphery of the dendritic or hyperbranched bis-MPA polymer.

There is also provided a co-polymer comprising a water soluble linear backbone polymer which is a two-armed polyethylene glycol (PEG), said PEG in each end thereof, i.e. in each arm, comprising a dendritic or hyperbranched polymer having at least one functional group comprising a carboxylic amine covalently attached to the periphery of the dendritic or hyperbranched polymer. Said water soluble linear backbone polymer may also be e.g. three or four armed having in each end a dendritic or hyperbranched polymer having at least one functional group comprising a carboxylic amine covalently attached to the periphery of the dendritic or hyperbranched polymer.

Said two-armed, three-armed or four-armed co-polymer as described herein may comprise from 32 up to 512 functional groups comprising a carboxylic amine, such as 32, 64, 128, 256, 384 or 512 functional groups, particularly 256 functional groups.

In one method for preparing the co-polymers of the present disclosure high functionality monomers may be used. These monomers display a higher number of functional groups than conventional $AB_2$ or $AB_3$ monomers. By using such high functional $AB_4$ (or $AB_8$) monomers, it is possible to obtain co-polymer (dendrimers) possessing a higher number of functional groups in fewer generations. By using such an approach, herein, a certain functionality of the co-polymer may be achieved using lower generations. As an example, the co-polymer PEG20k-G6-$(NH_3+)_{128}$, as a DLD (two-armed) possesses 256 functional groups. Such functionality may also be achieved by a lower generation co-polymer, but incorporating monomers with a higher functional density than an $AB_2$ monomer.

Herein, polymers comprising higher generations or higher functional density of dendritic or hyperbranched polymers have presented particularly advantageous properties in the context of the present disclosure. Therefore it is provided herein a polymer as defined elsewhere herein, wherein said dendritic or hyperbranched polymers are of generation 4 to 6 (G4 to G6), such as of generation 4, 5, or 6 (G4, G5, or G6). Particularly, said dendritic or hyperbranched polymers may be of generation 6 (G6). However, generations from G1 to G7 are also envisaged, i.e. G1, G2, G3, G4, G5, G6 and G7.

As previously mentioned, the periphery of the dendritic or hyperbranched structure of the co-polymer presented herein comprises a functional group comprising at least one carboxylic amine. However, more specifically the carboxylic amine may be a beta(β)-alanine. β-Alanine (beta-alanine) (IUPAC: 3-aminopropanoic acid) is a naturally occurring beta amino acid and a component of carnosine, anserine and pantothenic acid (vitamin B5). β-alanine has no stereocenter and is normally metabolized into acetic acid. The present disclosure also encompasses a functional equivalent of β-alanine, such as a synthetic variant, a derivative or an analogue thereof.

Possible modifications to the functional group comprising a carboxylic amine, such as to beta(β)-alanine may be performed by the addition of one or more of the same or of different carboxylic amines, e.g. by the addition of further of the same or of different amino acids or by performing other chemical modifications thereto. Examples of carboxylic amines useful in the context of the present disclosure have been presented elsewhere herein.

Co-polymers as disclosed herein, may be synthesized between PEG and bis-MPA from the first to the sixth generation, or even higher generations, such as with a PEG10k and a PEG20k linear component, or as otherwise disclosed herein. A conventional divergent growth approach using anhydride mediated esterification can be used to produce materials with from 4 up to 126 peripheral hydroxides centered around a linear PEG component. The co-polymer may then be converted from neutral hydroxides into a cationic nature to attain the desired effect Amine functionality was selected as the amino acid 13-Alanine. By utilizing e.g. tert-butyloxycarbonyl protecting group (BOC) protective chemistry, from the third to the sixth LD-co-polymer where converted to cationic amine functionality displaying from 32 to 126 amines per molecule.

Other methods of producing the materials herein are also envisaged. Notably, DLD- and LD-co-polymers comprising of PEG and bis-MPA were proven particularly useful herein e.g. due to biodegradability, biocompatibility and the design freedom. Accordingly, there is also provided herein a polymer, wherein said water soluble linear backbone polymer is PEG with a molecular weight of 20 kDa, such as about 10 to 20 kDa, wherein said dendritic or hyperbranched polymer is a (bis-MPA) generation 6 (G6), and wherein said at least one functional group comprising a carboxylic amine is β-Alanin, also referred to as "PEG20K-G6-β-Alanin". Said polymer may also be two-armed, in which it is sometimes, but not necessarily referred to as "(β-Alanin-G6)-PEG20K-(G6-β-Alanin)". It may also be referred to as PEG20k-G6-$(NH_3^+)_{128}$. As mentioned elsewhere herein, the co-polymer may also be three-armed or four-armed.

There is also provided herein the following polymers:
PEG20k-G4-$(NH_3^+)_{32}$
PEG20k-G5-$(NH_3^+)_{64}$
PEG10k-G4-$(NH_3^+)_{32}$,
PEG10k-G5-$(NH_3^+)_{64}$
PEG10k-G6-$(NH_3^+)_{128}$ More specifically, when presented with amine functionality in the form of β-Alanin there is provided herein the following co-polymers: PEG10K-(G4-β-Alanin), PEG10K-(G5-β-Alanin), PEG10K-(G6-β-Alanin), PEG20K-(G4-β-Alanin), PEG20K-(G5-β-Alanin) and PEG20K-(G6-β-Alanin). As mentioned elsewhere herein, hyperbranched variants are also envisaged which may also be referred to herein as PEG20k-hb-G4-$(NH_3^+)_{32}$, PEG20k-hb-G5-$(NH_3^+)_{64}$, PEG20k-hb-G6-$(NH_3^+)_{128}$, PEG10k-hb-G4-$(NH_3^+)_{32}$, PEG10k-hb-G5-$(NH_3^+)_{64}$ and PEG10k-hb-G6-$(NH_3^+)_{128}$. Also for the hyperbranched variants, $NH_3^+$ (amine) functionality may be provided by the amino acid β-alanin.

Further examples of co-polymers suitable for use in the context of the present disclosure comprise PEG2K-G4-$(NH_3^+)_{32}$, PEG2K-G5-$(NH_3^+)_{64}$, PEG2K-G6-$(NH_3^+)_{128}$, PEG5K-G4-$(NH_3^+)_{32}$, PEG5K-G5-$(NH_3^+)_{64}$, and PEG5K-G6-$(NH_3^+)_{128}$, or hyperbranched (hb) variants thereof. More specifically, when $NH_3^+$ (amine) functionality is provided by the amino acid β-alanin said co-polymers may be referred to as PEG2K-(G4-β-Alanin), PEG2K-(G5-β-Alanin), PEG2K-(G6-β-Alanin), PEG5K-(G4-β-Alanin), PEG5K-(G5-β-Alanin) and PEG5K-(G6-β-Alanin), including hyperbranched variants thereof also referred to herein as PEG2K-(hb-G4-β-Alanin), PEG2K-(hb-G5-β-Alanin), PEG2K-(hb-G6-β-Alanin), PEG5K-(hb-G4-β-Alanin), PEG5K-(hb-G5-β-Alanin) and PEG5K-(hb-G6-β-Alanin).

Figure 2:
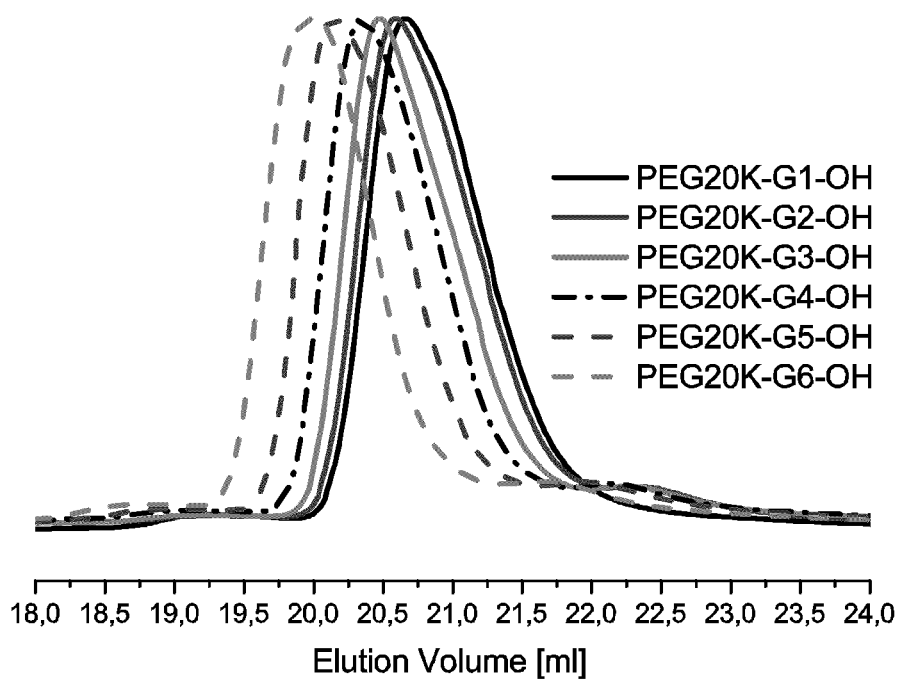
FIG. 2 are SEC curves for PEG20K-G1-OH to PEG 20K-G6-OH, displaying increasing hydrodynamic volume as a function of dendritic generation.

As previously mentioned herein, amine functionality $(NH_3^+)$ may be provided by β-Alanin. Two-armed, as well as three-armed and four-armed co-polymers are encompassed by the present disclosure. Notably, materials synthesized conformed to structure, and the thermal properties varied with the size of the dendritic block with crystallinity diminishing towards higher generation dendritic block. The structural evaluation of produced materials where conducted using $^1H$, $^{13}C$-NMR in combination with MALDI-TOF-MS and SEC analysis (FIG. 2). NMR yielded spectra conforming to structure (data not shown). Analysis using SEC reveled similar trend where molecular weight increases with generation, also here a miniscule amount of smaller sized PEG can be seen, (FIG. 2). Hydrodynamic volume increases with increasing generation and molecular weight, further confirming the structures where attained.

To enable the formation of an antibacterial composition in the form of a hydrogel comprising a co-polymer as disclosed herein, some of the functional amines of the periphery of the dendritic or hyperbranched polymers were used for cross-linking. The cross-linker has to fulfill a few requirements; I. It has to be biocompatible. II. Soluble in water and miscible with the active scaffold. III. Able to form cross-links with a primary amine. IV. Offer moduli in the range of surrounding tissue. Based on the criteria stated above a few candidates where identified, all candidates where based around a PEG with a molecular weight of 10 kDa based on previous work in terms of miscibility, compatibility, biocompatibility and moduli. However, as explained herein, other variants are also envisaged and thereby encompassed by the present disclosure.

Four cross-linking chemistries were then identified as fulfilling the demands above and to be of use in the context of the present disclosure, Carbonates (1), N-hydroxysuccinimide (NHS)(2), Imidazole activated acid (3) and ionic cross-linking using carboxyl groups (4). Other approaches using e.g. copper(I)-catalyzed azide-alkyne cycloaddition, thiol-ene chemistry are also envisaged to be of use herein.

Initial evaluation with regards to cross-linking was performed by mixing cross-linker and active substance PEG20K-G6-$(NH_3^+)_{128}$ in a 16:1 ratio with eventual addition of base to pH 7.4 deprotonating the amines. Cross-linkers 2-3 all rely on covalent linkage making gels formed more stable, both 2 and 3 both have byproducts from the cross-linking reaction however both are biocompatible. Cross-linker 4 provides covalent bonds without by-products which is useful for many biological applications, but reactivity was low. Cross-linker 3 proved highly active but reacted with the surrounding water. The evaluation of cross-linker 2 proved it to be cross-linking in water at physiological pH within seconds upon mixing the reaction preceded above the gel-point forming homogeneous gels, therefore cross-linker 2 denoted PEG10K—NHS (N-hydroxysuccinimide) is particularly preferred for cross-linking in the context of an exemplified hydrogel herein, although variants thereof including e.g. PEG of other molecular weights are also encompassed.

Accordingly, as described above, a cross-linker based on polyethylene glycol (PEG) possessing characteristics to react with amines was identified as particularly useful as a cross-linker for the hydrogel according to the present disclosure. N-hydroxysuccinimide (NHS) esters were preferred for due to their highly reactive nature under biological conditions. NHS chemistry is widely used in biomedicine due to its high degree of selectivity in reacting with primary amines and it is an activation of an acid substituting the hydrogen to a better leaving group mediating a nucleophilic attack on the carbonyl. NHS chemistry proceeds in most organic solvents under base catalysis but most importantly in water and better at physiological conditions.

Thus, there is provided herein a composition comprising a co-polymer as further described herein. Notably, said composition may comprise different polymers as described herein, i.e. a mixture of polymers of various dendrimer/hyper branched generations and comprising variants of the water-soluble linear backbone.

Said composition is particularly in the form of a hydrogel when said composition comprises a cross-linking agent. Accordingly, the composition, or hydrogel comprising said co-polymer, may further comprise a cross-linking agent. When it is referred to herein that a composition comprises at least two or more than one co-polymer(s) or individual polymers, or the like, this simply means that more than one co-polymer is involved in the formation of a hydrogel when the co-polymer is mixed or put in contact with the cross-linking agent to form a composition or hydrogel as mentioned herein. The cross-linking agent may comprise or be polyethylene glycol (PEG), such as PEG having a molecular weight within the range of 0.5 kDa to 50 kDa or 1 kDa to 50 kDa, such 10 kDa to 50 kDa, 5 kDa to 20 kDa, 10 kDa to 30 kDa, 10 kDa to 25 kDa, 10 kDa to 20 kDa, 20 kDa to 50 kDa, such as 0.5, 1, 5, 10, 20, 30, 40, or 50 kDa such as about 10 kDa. A PEG molecule of 10 kDa may be abbreviated herein as "PEG10k". More particularly, the cross-linking agent may comprise N-hydroxysuccinimide (NHS) for coupling to the functional groups of the dendritic or hyperbranched polymer. An example of a cross-linking agent is a 10 kDa PEG molecule covalently bound to NHS (PEG10K—COO—NHS or NHS—COO-PEG10K—COO—NHS). As shown herein, the later was proven to a successful candidate for providing a hydrogel comprising a cross-linked dendritic or hyperbranched co-polymer according to the present disclosure.

Said composition or hydrogel may also comprise one or more additional ingredients such as one or more organic plasticizers, buffers, salt ions, active pharmaceutical ingredients, surfactants, antiseptics and other polymers or monomers or the like. As mentioned previously herein, said composition may be in the form of a biodegradable hydrogel.

Generally, said hydrogel comprises about 1 to 100 weight % of cross-linked co-polymer, such as within the range of 1 to 15 weight %, or within the range of 2 to 10 weight %, and remaining water and/or other additional ingredients. Generally, a solution comprising an uncross-linked co-polymer comprises uncross-linked co-polymer in an amount of about 5 to 15 weight % in a buffer at the isoelectric point of the co-polymer. Generally a solution comprising a cross-linking agent comprises a cross-linking agent in an amount of 5 to 15 weight % in water.

Figure 3:
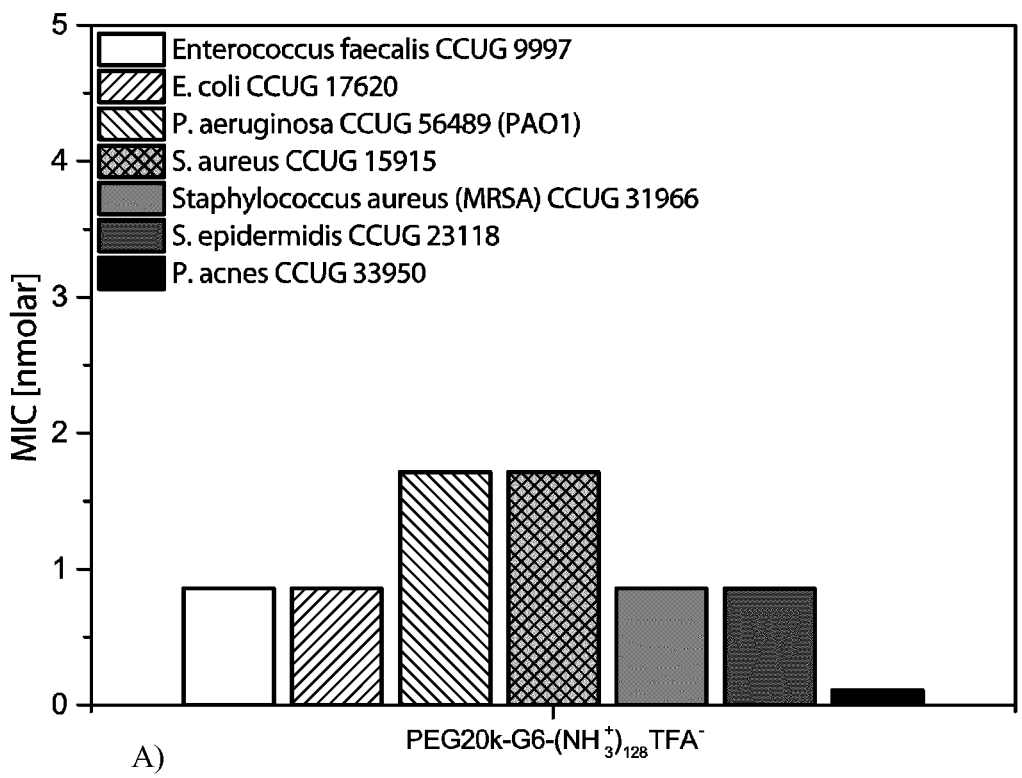
FIG. 3: Bio evaluation in solution with various bacteria. A) A MIC assay for uncross-linked co-polymer PEG20k-G6-$(NH_3^+)_{128}$ against various bacteria. B) MMC assay for uncross-linked co-polymer PEG20k-G4-$(NH_3^+)_{32}$ PEG20k-G5-$(NH_3^+)_{64}$ and PEG20k-G6-$(NH_3^+)_{128}$ against bacteria commonly found in an SSI (Surgical Site Infection).
Figure 3:
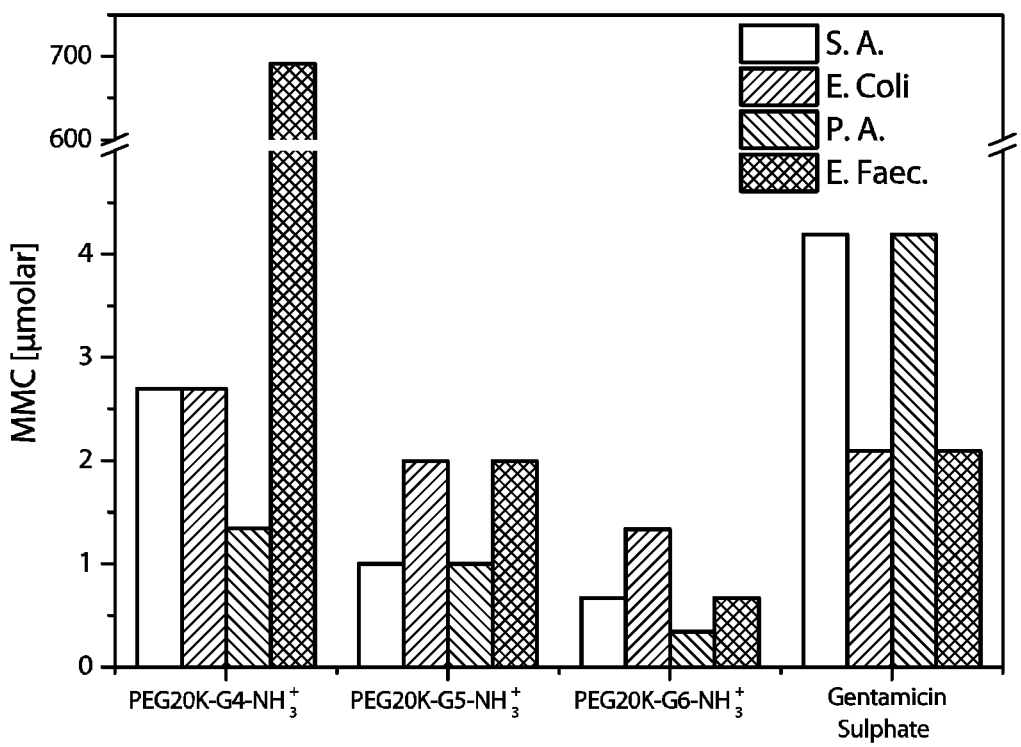
Figure 6:
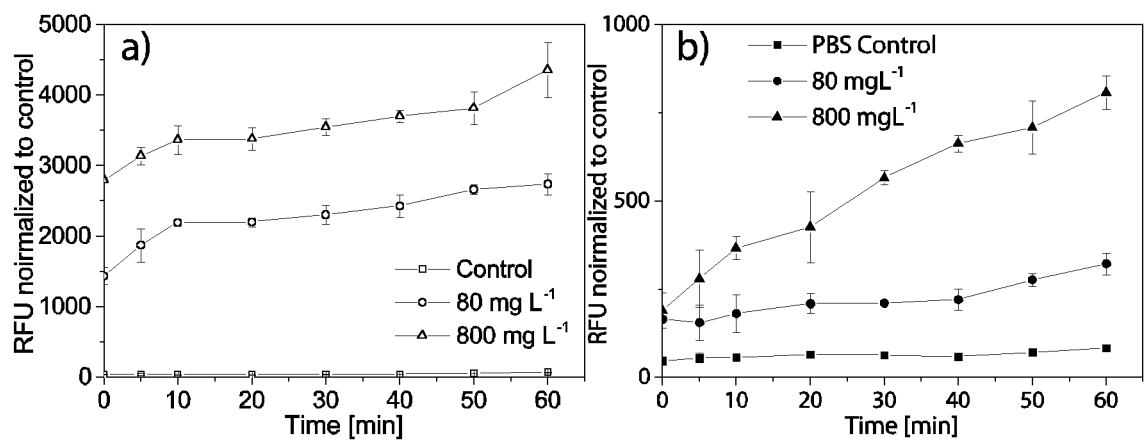
FIG. 6: a) Membrane disruption as measured by loaded fluorescent release caused by uncross-linked co-polymer PEG20k-G6-$(NH_3+)_{128}$ in *Escherichia Coli* (*E. coli*). b) Membrane disruption as measured by loaded fluorescent release caused by uncross-linked co-polymer PEG20k-G6-$(NH_3+)_{128}$ in *Staphylococcus Aureus* (*S. aureus*).

As previously mentioned herein, there is also provided herein the co-polymer, composition, or the hydrogel as defined herein, for use in a method of medical treatment or for use as a medicament. As an example, such a use or method comprises e.g. the protection of tissue surfaces or medical implants, such as prostheses for implantation into the human or animal body. Furthermore, there is provided for the use thereof in the treatment and/or prevention of a bacterial infection, wherein said treatment and/or prevention of a bacterial infection may comprise preventing or inhibiting growth or colonization of bacteria on said surface, such as a tissue or wound surface. Particularly, it is intended to be used in the prevention of a bacterial infection. Said treatment and/or prevention may comprise applying a suitable coating or the like of said composition or co-polymer onto a body surface, such as a tissue or a wound surface, to prevent growth or colonization of bacteria on said surface. The coating may be formed by spraying, utilizing a suitable device, the composition or hydrogel onto a damaged surface or onto a healthy surface for preventive purposes. The wound surface may be any wound surface, such as a burn wound surface, or a surface damaged in any other manner. The bacterial infection may be caused by a gram negative or a gram positive bacteria, such as by *Staphylococcus aureus, Pseudomonas aeruginosa, Escherichia coli* and/or *Enterococcus faecalis, Staphylococcus epidermidis*, and *Propionibacterium acnes*. The co-polymer or composition mentioned herein may also form part of, and/or be coated or sprayed onto, a wound dressing, plaster, band aid, or the like, to be applied to or attached onto a body surface, such as a tissue or a wound surface. As shown in FIGS. 3 and 6, both the uncross-linked and the cross-linked co-polymer are capable of preventing or at least inhibiting bacterial growth.

There is also provided a method of treating and/or preventing a bacterial infection in an individual in need thereof, said method comprising administering a pharmaceutically effective amount of a co-polymer, composition or a hydrogel according to the present disclosure and as described elsewhere herein to a tissue or a wound surface, such as to prevent growth or colonization of bacteria on said body surface. Said tissue or wound surface may be a site that is particularly exposed or vulnerable to a bacterial infection, or as described elsewhere herein.

Accordingly, particularly it is intended to apply the composition, hydrogel or the co-polymer topically, or similarly, to a surface in need of said treatment and/or prevention of a bacterial infection. The surface may be a body surface of a human or animal, wherein said surface comprises a wound or where a surgical incision has been made during a surgical procedure (SSI-Surgical Site Infection) increasing the risk of a bacterial infection in said area. The surface may also be a surface of a medical device, such as a medical implant, where treatment of the surface is performed before the implant is introduced into the human or animal body to prevent that any bacteria adhere and/or grow on the surface of the medical implant or at a later stage. Hence, there is provided a use of the composition, co-polymer or hydrogel as disclosed herein for the pre-treatment of a surface of a medical implant, by applying said composition to at least a part of a surface of said medical implant.

There is also more specifically provided herein a co-polymer comprising a water soluble backbone polymer having in at least one end a dendritic or hyperbranched polymer, wherein said dendritic or hyperbranched polymer is of generation 6 (G6) and wherein at least one functional group comprising a carboxylic amine is covalently attached to the periphery of the dendritic or hyperbranched polymer, wherein said co-polymer is selected from the group consisting of PEG20k-G6-$(NH_3^+)_{128}$, PEG10k-G6-$(NH_3^+)_{128}$, PEG5k-G6-$(NH_3^+)_{128}$, and PEG2k-G6-$(NH_3^+)_{128}$. More specifically said dendritic or hyperbranched polymer may comprises the monomer 2, 2-Bis(hydroxymethyl)propionic acid (bis-MPA). Even more particularly, co-polymer may be selected from the group consisting of PEG10K-(G6-β-Alanin) and PEG20K-(G6-β-Alanin), PEG5K-(G6-β-Alanin) and PEG2K-(G6-β-Alanin), or a hyperbranched variant thereof.

There is also provided a kit of parts comprising: a) a dispenser comprising a co-polymer or a composition comprising a polymer as defined anywhere herein; and b) a dispenser comprising a cross-linking-agent. Said co-polymer is any dendritic or hyperbranched co-polymer as previously disclosed herein. Said cross-linking agent may comprise or be a polyethylene glycol (PEG) as defined herein, such as PEG having a molecular weight of about 10 kDa (abbreviated "PEG10k"). More particularly, the cross-linking agent may comprise or be N-hydroxysuccinimide (NHS) for coupling to the functional groups of the dendritic or hyperbranched polymer. An example of a cross-linking agent is a PEG of 10 kDa covalently bound to NHS (NHS—COO-PEG10K—COO—S, also sometimes referred to as PEG10K—COO—NHS).

Accordingly, the kit of parts comprises a two component system comprising two separate means or devices for delivery of the (uncross-linked) co-polymer and the cross-linking agent, respectively. It is of great relevance that the contents of the two components are kept separate until such a use is intended. The dispenser(s) may be equipped so as to deliver the contents therein as a spray (a "spray-able device") or the like. This would be particularly suitable for topically applying a gel coating as previously disclosed herein. Herein, a dual syringe application system was purchased from Medmix® called Twin-Syringe Biomaterial Delivery System (M-System) that was optimized for delivery of antibacterial hydrogel. Syringe system offers spray, air assisted spray and spreader application, the latter was selected since well-defined homogeneous films where attained. The kit of parts may also comprise instructions for use.

Accordingly, there is also provided herein a method for coating a surface of an human or animal body, such as a tissue surface exposed during surgery or a wound surface, with a composition comprising a cross-linked co-polymer as disclosed herein, said method comprising the steps of mixing an solution comprising an uncross-linked co-polymer as disclosed herein with a cross-linking agent, also disclosed herein, to yield a hydrogel comprising a cross-linked co-polymer, and thereafter applying a coating of said hydrogel comprising said cross-linked co-polymer onto said surface, wherein the mixing is performed e.g. no more than about 10 minutes before the hydrogel is to be applied to said surface, such as from within a few seconds to a few minutes from mixing the components. The surface may also be a surface of a medical implant or equipment used during surgery, as previously mentioned herein. Preferably, the hydrogel coating is applied so that it substantially covers the surface concerned, e.g. a wound, to prevent bacteria to spread or colonize. Said coating preferably has as a thickness of no less than 50 μm and up to about 400 μm, but is not limited thereto. As shown in FIG. 6, such a coating was able to substantially inhibit bacterial growth.

There is also provided the use of a co-polymer as defined herein, a composition as defined herein or the kit as defined herein for the treatment or pre-treatment of a surface of a medical implant, by applying said composition or co-polymer to at least a part of a surface of said medical implant. Said treatment or pre-treatment may have the effect of a protective coating presenting a barrier to colonization or growth of bacteria on said surface.

There is also provided the use of a co-polymer as defined herein in a composition comprising a cross-linking agent as defined anywhere herein. The subsequent use of the composition is described elsewhere herein.

Optimizations to attain reliable antibacterial hydrogels for a delivery system (kit of parts) presented herein were performed, involving evaluation of cross-linking agent and cross-linking agent stability, degradation of the hydrogel etc. As an example, to attain gels for a system comprising of PEG20K-G6-β-$(NH_3^+)_{128}$ and PEG10K—COO—NHS with $NaHCO_3$ in water, optimization was performed. If components are mixed together gelation would occur within seconds making it physically impossible to transfer mixture to desired location before they cross-link. Components should preferably be kept separately until the last seconds and mixed just prior to application. Since there are 128 amines on PEG20K-G6-$(NH_3^+)_{128}$ and as many as possible should be maintained for maximal antibacterial effect it was chosen to evaluate 4, 8, 16 and 32 cross-links per material. Base was added to the stock solution containing PEG20K-G6-$(NH_3^+)_{128}$, to remove the TFA counter ion making the primary amines available to react with the NHS-ester. For mechanical evaluation the natural choice was rheology, as we are studying the transition from a liquid to a solid. For these measurements micropipettes are sufficient to apply the two stock solutions. However, for biological evaluation a different method had to be developed due to the large volumes of sample that needs to be applied relatively quickly.

The modulus readings after gelation was considerably reduced after just 15 minutes post addition of water to form stock solutions (PEG20K-G6-$(NH_3^+)_{128}$ and PEG10K—COO—NHS). However, if a freshly prepared stock solution of PEG10K—COO—NHS was prepared the modulus returned to its original value. This indicated that PEG10K—COO—NHS degraded in a water solution, most likely through hydrolysis of the NHS-ester. Indications were in line with literature stating that NHS stability decreases with increasing pH. Hydrolysis rate in water was investigated by $^1$H-NMR for PEG10K—COO—NHS. Rate of hydrolysis is initially very high and 30% of the NHS-esters are hydrolyzed within 10 minutes, followed by a seemingly plateauing trend. Without wishing to be bound by theory, the fact that hydrolysis rate decrease with time is probably due to the formation of acids upon hydrolysis, lowering the pH and thus the reactivity.

Cross-linking evaluation was performed in real time using rheology. Cross-linking and final modulus between PEG20K-G6-$(NH_3^+)_{128}$ and PEG10K—COO—NHS (4, 8, 16 and 32 amines out of 128 were used for cross-linking). By varying the amount of cross-links modulus in the range from brain, lung and fat tissue all the way up to cartilage could be obtained. Cross-linking time was inversely proportional to amount of cross-linkers while modulus was proportional to amount of amount of cross-links. Looking at the amine content theoretically calculated as $mM/mm^2$ the gain in modulus going from 8 to 16 is generally not worth the considerable decrease of amine content for a minimal decrease in cross-linking time 50 instead of 55 and modulus increase of 1 kPa. While going from 4 to 8 provides quicker cross-linking time 55 instead of 90 seconds and a considerable increase in modulus validating the decrease in amine content. This makes 8 a very useful cross-linking ratio maintaining high amine content while providing sufficient modulus and short enough cross-linking time.

Accordingly, the amount of cross-linking agent added to the co-polymer will be so that after cross-linking has occurred between the co-polymer(s) and the cross-linking agent there are still amines available for providing an antibacterial effect, as further explained herein. As an example, to PEG20K-G6-(NH$_3^+$)$_{128}$, comprising 128 free amine groups, it was tested to use 4, 8, 16 and 32 amines out of 128 amines for cross-linking. This means that after cross-linking, 124, 120, 112, and 96 amines were still free and able to exert the antibacterial effect. Hence, the amount may be such that the molar ratio between the crosslinking functional groups on the cross-linking agent and the carboxylic amines of the co-polymer are in the range of 1:4 to 1:64, 1:4 to 1:32, such as 1:64, 1:32, 1:16; 1:8, or 1:4, preferably about 1:16 to 1:32.

The length of the linear (PEG) segment for both the active amine functional scaffold and the cross-linker was then varied, 15 amine functional DLD as well as three different length of the cross-linker (2 k, 6 k and 10 k) was used to effectively vary the average distance between cross-links. The length between cross-links should preferably be proportionate to the density of amines in the gel. Decreasing the length of the linear part of the dendritic block appears to result in an expected higher modulus while decreasing the length of the cross-linker resulted in a lower modulus. This could be due to intramolecular instead of intramolecular cross-links forming when the length of the cross-linker decreases resulting in loops.

Degradation of the antibacterial hydrogels is of importance since the gel preferably needs to remain stable during the desired time period of between 6 to 24 hours actively inhibiting bacterial growth. Degradation occurs from the pheriphery by first hydrolysis of the functionality, i.e. the β-Alanin followed by depolymerization of the bis-MPA backbone. Degradation seems to occur and it appears to be able to detect as a function of decreasing storage modulus.

The invention will now be exemplified by virtue of the experimental section but it is not intended to be limited thereto.

EXPERIMENTAL SECTION

Synthesis of Polymers

General Example

Polymers comprising linear PEG and two dendritic blocks bis-MPA were synthesized (DLD) Bis-MPA based dendritic structures were grown from the hydroxyl terminus of the PEG segment. To provide antibacterial properties the resulting DLD were converted to amine functionality.

General Procedure for DLD Synthesis.

A conventional divergent growth approach was used for construction of dendritic blocks. Anhydride mediated esterification was employed for growth using DMAP as catalyst, pyridine to maintain basic conditions and dichloromethane as solvent. Using an optimized ratio between hydroxyls, pyridine and DMAP of [1]:[3]:[0.2] resulted in fully substituted dendritic blocks. Acetonide protective chemistry was utilized and activation was performed using Dowex w50 (100 wt %) in MeOH. Progression of both growth and activation steps was monitored by $^1$H, $^{13}$C-NMR as well as MALDI-TOF-MS. Growth and activation steps were repeated in sequence until the desired structure was obtained.

General Growth Procedure.

Hydroxyl functional polymer was dissolved in dichloromethane and pyridine (3 eq. per OH) at a concentration between 1 and 0.1 molar in a round bottom flask equipped with magnetic stir bar. DMAP (0.2 eq. per OH) was added and the reaction cooled to 0° C. using an ice bath. Bis-MPA anhydride was slowly added to the reaction mixture. The vessel was subsequently sealed using a septum and allowed to proceed for 14 h under vigorous stilling and monitored using $^1$H, $^{13}$C-NMR and MALDI-TOF-MS. Upon completion the concentration of the crude reaction mixture was adjusted to approximately 1 g mL$^{-1}$ and precipitated twice in cold di ethyl ether (100 mL g$^{-1}$)

General Activation Procedure.

The acetonide protected structure was dissolved in MeOH at a concentration of 1 mM in a round bottom flask equipped with magnetic stir bar. Dowex W50 (100-150 wt %) was added to the reaction vessel and it was sealed using a septum. The reaction was allowed to proceed for 1 h under vigorous stilling and the progression monitored by $^1$H-NMR (400 MHz, CDCl$_3$): δ (ppm) 1.43, 1.38) and MALDI-TOF-MS. The crude reaction mixture was filtered and the Dowex w50 thoroughly washed with MeOH. The filtrate was evaporated to dryness. This procedure was repeated until complete deprotection was observed. Upon completion the concentration of the crude reaction mixture was adjusted to approximately 1 g mL$^{-1}$ and precipitated twice in cold di ethyl ether (100 mL g$^{-1}$).

Functionalization of Polymeric Scaffolds

This disclosure deals with functional polymers and while many approaches have been used to attain functional materials, the two most common methods are anhydride and FPE chemistries, both are detailed below.

General Procedures for Functionalization of Endgroups

Two main approaches where used:
1. Functionalization with anhydride growth step, described above.
2. Functionalization using fluoride promoted esterification (FPE) Acid functional monomer (1-1.5 eq. per OH on hydroxyl functional scaffold) was reacted at 50° C. for 1 h with 1 eq. of CDI in EtOAc (1 M) in a round bottom flask sparged with argon. The conversion to activated imidazolide was monitored by $^1$H-NMR (400 MHz, Chloroform-d) δ 10.31 (Imidazole NH) 8.15 (t, J=1.1 Hz, Imidazolide N=CH$_2$—N), 7.66 (t, J=1.1 Hz, Imidazole N=CH$_2$—N), 7.44 (t, J=1.5 Hz, 1H Imidazolide CH$_2$=CH$_2$—N), 7.07 (d, J=1.1 Hz, Imidazole and imidazolide N—CH$_2$=CH$_2$), and is usually close to 100%. Upon completion, hydroxyl functional polymer scaffold was added along with CsF (0.2 eq. per OH on hydroxyl functional scaffold) and the reaction vessel was sealed with a septum and allowed to proceed until completion as monitored by $^1$H-, $^{13}$C-NMR and MALDI-TOF-MS. Upon completion water was added and the reaction allowed to proceed under vigorous stirring until devoid of active monomer as monitored by $^1$H-NMR. The reaction was subsequently diluted to approximately 0.1 g mL$^{-1}$ in EtOAc and the organic phase washed trice with aqueous NaHSO$_4$ (10 wt %), aqueous NaCO$_3$ (10 wt %) and brine once (10 v % based on organic phase). The resulting organic phase was dried with MgSO$_4$, filtered and evaporated to dryness. The product was then used as is or purified by column chromatography as required.

Specific Examples

Growth from PEG20K-G5-OH to PEG20K-G6-Acet

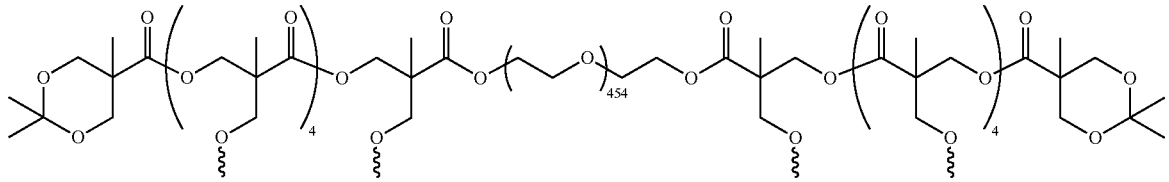

In a round bottom flask equipped with a magnetic stirrer was PEG20K-G5-OH (19.0 g, 0.69 mmol) dissolved in 14 mL of DCM and Pyridine (10.8 mL, 134 mmol). DMAP (1.64 g, 13.4 mmol) was added and acetonide protected bis-MPA anhydride (29.5 g, 89.4 mmol) was added to the reaction under vigorous stirring. The reaction was allowed to proceed for 14 hours and monitored by $^{13}$C-NMR and $^{1}$H-NMR as well as MALDI-TOF-MS. Upon completion the crude reaction was precipitated three times in cold ether, the product was isolated by filtration as a white fluffy, a bit sticky, powder (23.0 g, 88.5%). $^{1}$H NMR (400 MHz, Chloroform-d) δ 4.30 (dq, J=21.7, 11.7 Hz, 245H), 4.15 (d, J=11.7 Hz, 134H), 3.67 (s, 1611H), 1.39 (d, J=26.0 Hz, 385H), 1.29 (d, J=4.6 Hz, 217H), 1.16 (s, 192H). $^{13}$C NMR (101 MHz, CDCl$_3$) δ 173.17, 171.57, 171.18, 171.06, 170.95, 97.79, 70.36, 65.68, 64.93, 64.45, 46.55, 46.39, 41.77, 25.00, 21.88, 18.28, 17.51, 17.32, 17.19, 16.98. MALDI$_{calc}$ [M+Na$^+$]=40165.6 Da, Obtained [M+Na$^+$]=40174.74 Da. SEC (DMF) M$_n$=23680 g mol$^{-1}$, Đ=1.0465.

Activation from PEG20K-G6-Acet to PEG20K-G6-OH

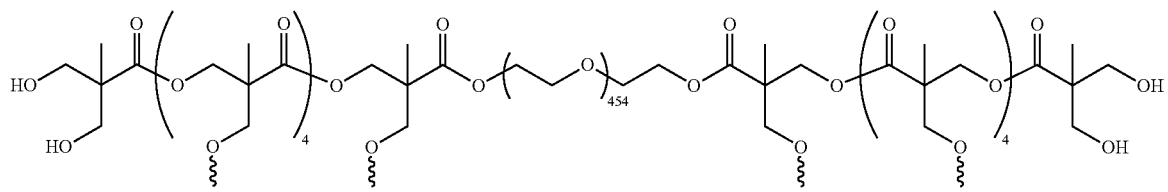

In a round bottom flask with magnetic stirring bar PEG20K-G6-Acet (22.0 g, 0.59 mmol) was dissolved in 600 mL MeOH and Dowex™ (200 g) was added and reaction was allowed to proceed one hour. Progress was checked with $^{1}$H-NMR and acetonide protection groups was still observed. Dowex™ was filtered off and MeOH was evaporated. The crude PEG20K-G6-OH was redissolved in MeOH and 200 g reactivated Dowex™ was added. The procedure was repeated until no residual protective groups could be observed in $^{1}$H-NMR and MALDI-TOF-MS. MeOH was evaporated, the product was redissolved in DCM and precipitated in cold ether. Product collected as white fluffy, a bit sticky, powder after filtration (17 g, 83%). $^{1}$H NMR (400 MHz, Methanol-d$_4$) δ 4.45-4.18 (m, 252H), 3.64 (s, 1970H), 1.44-1.24 (m, 162H), 1.16 (s, 192H). $^{13}$C NMR (101 MHz, MeOD) δ 175.80, 173.71, 173.21, 173.09, 71.49, 69.83, 66.97, 66.82, 66.01, 65.78, 51.68, 48.06, 48.00, 47.95, 47.82, 18.44, 18.25, 17.44. MALDI$_{calc}$ [M+Na$^+$]=37610.26 Da, Obtained [M+Na$^+$]=37623.4 Da. SEC (DMF) M$_n$=26886 g mol$^{-1}$, Đ=1.04.

Functionalization from PEG20K-G6-OH to PEG20K-G6-β-Alanin-BOC

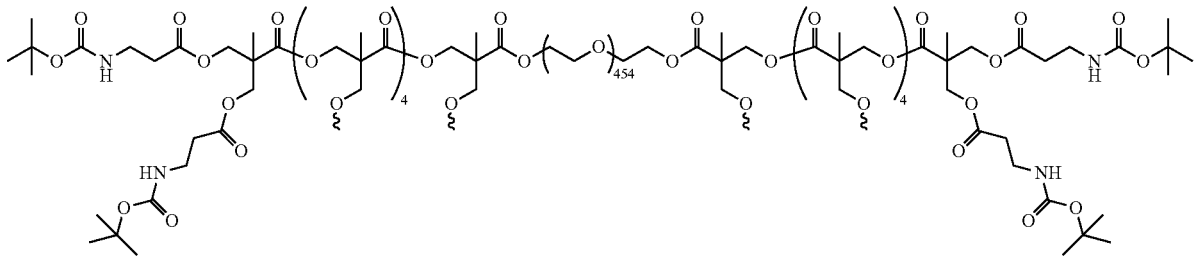

PEG20K-G6-OH (1 g, 28.9 μmol) was dissolved in pyridine (890 μL, 11.1 mmol) and 500 μL of chloroform in a round bottom flask equipped with magnetic stir bar. DMAP (90.3 mg, 0.74 mmol) and β-Alanin-BOC anhydride (2.00 g, 5.54 mmol) was added and allowed to react for 14 hours. Crude reaction mixture was precipitated in cold ether twice and product was collected as white powder (1.28 g, 78.4%) $^1$H NMR (400 MHz, Chloroform-d) δ 4.47-4.11 (m, 180H), 3.67 (s, 6695H), 3.46-3.35 (m, 288H), 2.57 (q, J=5.7 Hz, 256H), 1.45 (s, 1093H), 1.32-1.24 (m, 510H). $^{13}$C NMR (101 MHz, CDCl$_3$) δ 171.93, 171.66, 171.53, 171.50, 171.48, 171.37, 171.28, 155.80, 79.11, 70.50, 65.75, 64.67, 46.49, 46.32, 36.07, 34.34, 28.34, 17.76, 17.53, 15.21. SEC (DMF) M$_n$=32952 g mol$^{-1}$, Đ=1.06.

Activation from PEG20K-G6-Alanin-BOC to PEG20K-G6-β-Alanin$^+$ TFA$^-$ 8.45 g) was added along with pTSA (5 wt % of bis-MPA, totally 422 mg). During addition of bis-MPA, argon was flushed through the reaction vessel. When the desired generation had been reached one additional hour of argon flushing was applied after which vacuum was induced in the reaction vessel for 18 hours. The resin was extracted from the reaction vessel without further purification. The product 17 was collected as a yellow glassy solid. (85%, 14.7 g)$^1$H-NMR (400 MHz, CDCl3): δ (ppm) 4.29-3.81 (q, 252H, —CH$_2$—OCO—, (bis-MPA)), 3.62 (q, 1828H, CH$_2$—CH$_2$—O—, (PEG)), 1.23-1.05 (q, 372H, —CH$_3$, (Bis-MPA)). $^{13}$C-NMR (100 MHz, DMSO-D6): δ (ppm) 173.8-172.6 (1C, —COO—, (bis-MPA)), 69.71 (2C, CH$_2$—CH$_2$—O—, (PEG)), 63.6 (1C, —CH$_2$—, (bis-MPA)), 50.2 (1C, —COO—C—((CH$_2$—OH)$_2$, CH$_3$) (bis-MPA)), 49.5 (1C, —COOH—C—((CH$_2$—OR)$_2$, CH$_3$) (bis-MPA)), 48.1

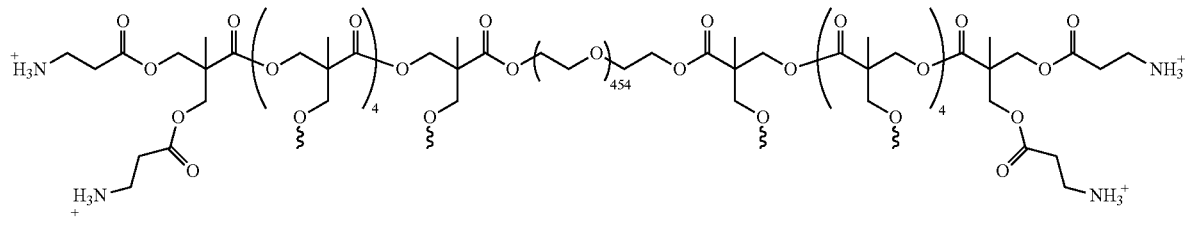

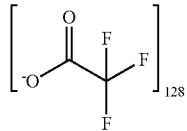

PEG20K-G6-β-Alanin-BOC (545 mg, 13.6 μmol) was dissolved in TFA (2 mL, 26.2 mmol) in a round bottom flask equipped with magnetic stir bar, the vessel was sealed with a septum with a needle to let out generated CO$_2$. Reaction was allowed to proceed for 1 hour and progress was monitored with $^1$H-NMR, upon completion the crude product was precipitated in ether twice and product collected as a white powder (551 mg, 69.7%). $^1$H NMR (400 MHz, Methanol-d$_4$) δ 4.32 (dd, J=22.4, 11.1 Hz, 499H), 3.67 (s, 1557H), 3.28 (d, J=6.9 Hz, 256H), 2.85 (t, J=6.8 Hz, 256H), 1.31 (d, J=11.1 Hz, 381H). $^{13}$C NMR (101 MHz, MeOD) δ 173.48, 173.28, 171.90, 163.06, 162.71, 162.36, 162.02, 71.31, 66.64, 47.92, 47.60, 36.41, 32.26, 18.37.

Synthesis of PEG20K-G6hb-OH

PEG20K—OH (0.50 mmol, 10.0 g) was added in a two necked round bottom flask equipped with argon inlet, magnetic stirrer and distillation equipment and heated to 130° C. Every sixty minutes bis-MPA equivalent to one increase in dendritic generation totally bis-MPA (126 eq, 63.0 mmol, (1C, —COO—C—(CH$_2$—OH, CH$_3$, CH$_2$—OR) (bis-MPA)), 46.2, 45.5 (1C, —COO—C—((CH$_2$—OR)$_2$, CH$_3$) (bis-MPA)), 16.7 (1C, —CH$_3$ (bis-MPA)).) SEC (Mw=19606 g/mol, Đ=1.55).

Synthesis of Cross Linker

Synthesis of PEG10K—COOH

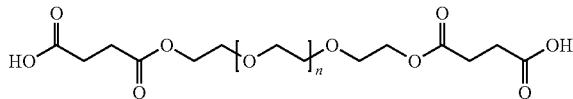

In a round bottom flask equipped with a magnetic stirrer PEG10K—OH (100 g, 10.0 mmol) was dissolved in pyridine (4.75 g, 60.0 mmol) and DCM 100 mL. DMAP (489 mg, 4.00 mmol) was added and under vigorous stirring succinic anhydride (3 g, 30.0 mmol) was slowly added as a powder. The reaction was allowed to proceed for 14 hours and the progression confirmed with $^{13}$C-NMR ($^{13}$C NMR (101 MHz, CDCl$_3$) δ (PPM)=170.6 (COO—COO)) and MALDI-TOF-MS. The crude reaction mixture was washed with aqueous NaHSO$_4$ (10 wt %) three times, dried filtered and precipitated in ether twice. Product was collected as a fluffy white powder (95.0 g, 93.2%)$^1$H NMR (400 MHz, Chloroform-d) δ 4.31-4.01 (m, 4H, O—CH$_2$—CH$_2$—COO—), 3.59 (s, 919HO—CH$_2$—CH$_2$—), 2.77-2.44 (m, 8H COO—CH$_2$—CH$_2$—COOH). $^{13}$C NMR (101 MHz, CDCl$_3$) δ 173.80, 172.23, 70.56, 69.00, 63.74, 29.47, 29.05. SEC (DMF) M$_n$=1430 g mol$^{-1}$, Đ=1.09

PEG10K—COO—NHS

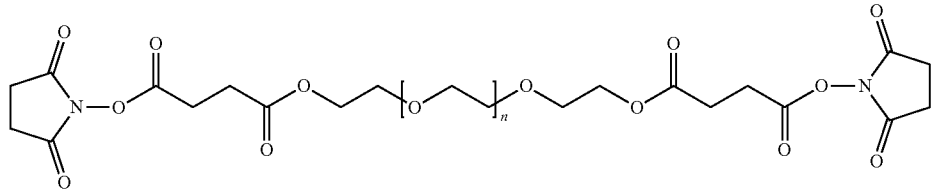

PEG10K—COOH (10 g, 0.98 mmol) was dissolved in 4 mL of DCM in a round bottom flask with a magnetic stirrer. Carbonyldiimidazole (3.2 g, 19.6 mmol) was slowly added under inert environment (Ar flow) and allowed to react for one hour at room temperature. N-Hydroxysuccinimide (2.7 g, 23.5 mmol) was added and the reaction was allowed to proceed for 14 hours. The crude reaction mixture was diluted to 50 mL of total volume with DCM and washed with NaHSO$_4$ two times. The organic phase was dried with MgSO$_4$, filtered and concentrated to a total volume of 5 mL and precipitated in ether. Product was collected as a fluffy white powder (4.5 g, 88.3%)$^1$H NMR (400 MHz, CDCl$_3$) δ 4.26 (t, J=4.7 Hz, 6H), 3.63 (s, 1480H), 2.95 (t, J=7.0 Hz, 4H), 2.82 (s, 8H), 2.76 (t, J=7.0 Hz, 3H). $^{13}$C NMR (101 MHz, CDCl$_3$) δ 171.06, 168.97, 167.77, 72.02, 70.70, 70.66, 70.61, 69.02, 64.30, 59.13, 53.56, 28.75, 26.35, 25.66. SEC (DMF) M=11724 g mol$^{-1}$, Đ=1.05.

Synthesis of Gel
Base Catalyzed NHS Chemistry

A series of gels were prepared in a rheometer, equipped with a Peltier plate-plate accessory, using a stainless-steel upper geometry (ø=20 mm) at a temperature of 34° C. The amine functional polymer was dissolved in water together with NaHCO$_3$ (amount eq. to a pH of 7.4 as determined by titration). The NHS cross-linker (4, 8, 16, 32 or 64 eq. per LD-co-polymer) was dissolved in a separate vial in Milli-Q water. Both components were deposited separately in the rheometer (final composition 10 wt-% solid) and mixed with a pre shear program of 30 rad/s for 3 seconds. Time sweeps were conducted at strain (Υ)=1% and frequency (ω)=1 Hz. To ensure all measurements were carried out in the linear viscoelastic region (LVR), complimentary frequency and amplitude sweeps were carried out from 0.01 to 100 rad/s and 0.01 to 100% strain. All measurements were performed in triplicates. Freestanding gels were done using the same solutions as mentioned above. They were either casted by drop casting, loaded into twin syringe biomaterial delivery system, M-System (Medmix) equipped with spreader tip (animal study and MMC, MIC assays) or a spray tip (spray testing). Gels were allowed to sit 60 seconds undisturbed before extracted or moved.

MMC$_{99}$ Assay

Minimal microbiocidal concentration (MMC) assay was preformed fot PEG20k-G4-(NH$_3^+$)$_{32}$ (38), PEG20k-G5-(NH$_3^+$)$_{64}$ (40), PEG20k-G6-(NH$_3^+$)$_{128}$ (42) using gentamicin sulfate as comparison, four different bacterial strains where used: *Staphylococcus aureus* (SA), *Pseudomonas aeruginosa* (PA)), *Escherichia coli* (*E. coli*) and *Enterococcus faecalis* (E. faec). Briefly, bacteria were transferred from the agar plates to 3.7% BHI using a sterile loop and cultured for 16 hours on a shaking table (250 rpm at 37° C.). The culture was diluted 1:10 in fresh BHI-medium and incubated for another 2 hours on a shaking table (250 rpm at 37° C.). The bacterial suspension was then centrifuged at 1000 g and the pellet was re-suspended in 0.037% BHI to a final concentration of approximately 10$^7$ colony forming units (CFU) mL$^{-1}$. A volume of 100 µl of each test item dilution was mixed with 5 µl bacterial suspension in the wells of a 96-well plate and incubated at 37° C. for two hours. Five µL of each suspension was added as drops in triplicate onto agar plates supplemented with 5% defibrinated horse blood, and incubated over night at 37° C. The minimal test item concentration causing 99% reduction of bacteria was defined as the MMC. The antimicrobial effect was found to increase in all strains with increasing dendritic generation going from approximately 3 µM for the 4$^{th}$ generation down to less than 1 µM for the 6$^{th}$ generation scaffold, the results are shown in FIG. 3a.

MIC Assay

The MIC value is defined as the concentration where 90% optical density reduction was observed. To each well 200 µL$^{-1}$ of each dilution in the desired dilution series of PEG20k-G6-(NH$_3^+$)$_{128}$ was added to a 96-well plate. To each well 100 µL$^{-1}$ of 10$^6$ CFU yielding a final CFU of 5×10$^5$ in each well. The plates were sealed with an adhesive plastic film and incubated at 36±1° C. for 24 hours and the optical density was then measured at 595 nm. Five bacterial strains where used: *Enterococcus faecalis* CCUG 9997 (ATCC 29212), *E. coli* CCUG 17620 (ATCC 25922), *P. acnes* CCUG 33950, *Pseudomonas aeruginosa* CCUG 17619 (ATCC 27853), *Pseudomonas aeruginosa* CCUG 56489 (ATCC 15692)=PAO1, *S. aureus* CCUG 15915 (ATCC 29213), *Staphylococcus aureus* (MRSA) CCUG 31966 and *S. epidermidis* CCUG 23118. The PEG20k-G6-(NH$_3^+$)$_{128}$ was found to have effect across the board of tested microbes with MIC values down in the single digit nanomolar range, the results are shown in FIG. 3b.

Cytotoxicity Assay

Figure 4:
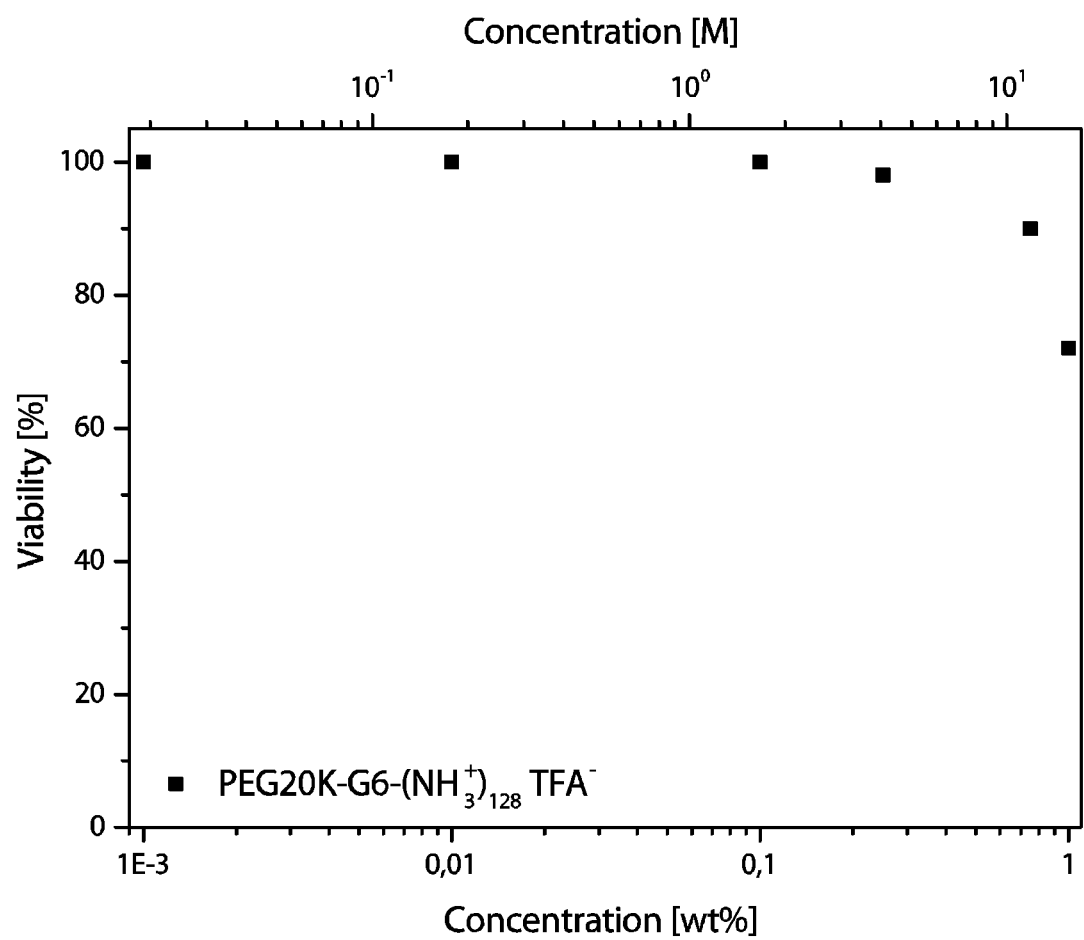
FIG. 4: Bio evaluation of uncross-linked co-polymer in solution. Cytotoxicity evaluation using VTS-1 assay for PEG20k-G6-$(NH_3^+)_{128}$ against mouse fibroblasts.

A subconfluent monolayer of L929 mouse fibroblast cells (NCTC clone 929: CCL-1 American Type Culture Collection) was used. The cell cultures are regularly checked for *mycoplasma* contamination. Aliquots of cells were stored at −150° C. and rapidly thawed at 37±1° C. in a water bath. The cells were then propagated in tissue culture flasks at 37±1° C. in 5±1% CO2 with Eagle's minimum essential medium (MEM) 1× with non-essential amino acids and sodium pyruvate, supplemented with 10% (v/v) Fetal Bovine Serum, 4 mM L-glutamine, 100 IU/mL penicillin and 100 µg/mL streptomycin. The cells were subcultured 3 times (after thawing) before 100 µL/1×10$^4$ cells were seeded per well in 96 well plates for the cytotoxicity test. The 96-well plates with cells were incubated for 24±2 hours at 37±1° C. n 5±1% CO2 to obtain a subconfluent monolayer of cells prior to exposure to the test items. Following incubation with test iteam, in this case PEG20k-G6-(NHO$_{128}$, 10 μl of WST-1 reagent was added to each well, the plates the n further incubated for 2 hours at 37±1° C. in 5±1% CO$_2$. Then the plate was shaken for about 1 minute, and finally absorbance 690 nm). The biocompatibility of PEG20k-G6-(NH$_3^+$)$_{128}$ was maintained up to 0.1 mM or slightly below 1 wt %, the results are shown in FIG. 4.

Membrane Permeability Assay

The assay was derived from T. A. Chitemerere, S. Mukanganyama, Bmc Complem Altern M 2014, 14. Briefly, bacteria expended in LB broth and collected during the exponential phase (4-5 h incubation at 37° C. with shaking). Bacterial cells were washed with PBS twice and inoculate ($10^{11}$ cell mL$^{-1}$) to PBS buffer containing 1 μM diSC3-5 for 1 h and 5 mM glucose. Bacteria were mixed with PEG20k-G6-(NH$_3^+$)$_{128}$ at the desired concentration PBS was used as negative control and 8% DMSO was used as positive control. 0.5 mL of sample was collected at desired time points (0, 5, 10, 20, 30, 40, 50, 60 min) and mixed with 0.5 mL PBS in Eppendorf tubes and centrifuged at 5000 rcf for 5 min. Then the supernatants (3×100 μL) was collected and transferred into 96-well black plates and the fluorescence was measured at 622/670 nm (ex/em) The resulting relative fluorescent intensity (RFU) was normalized to the same level native control. Both gram positive *Staphylococcus aureus* and gram negative *Escherichia coli* where used in this study. Upon exposure to PEG20k-G6-(NH$_3^+$)$_{128}$ release of the loaded fluorescent was observed indicating that the bacterial membrane was ruptured, results are shown in FIG. 6.

Rheology

Figure 5:
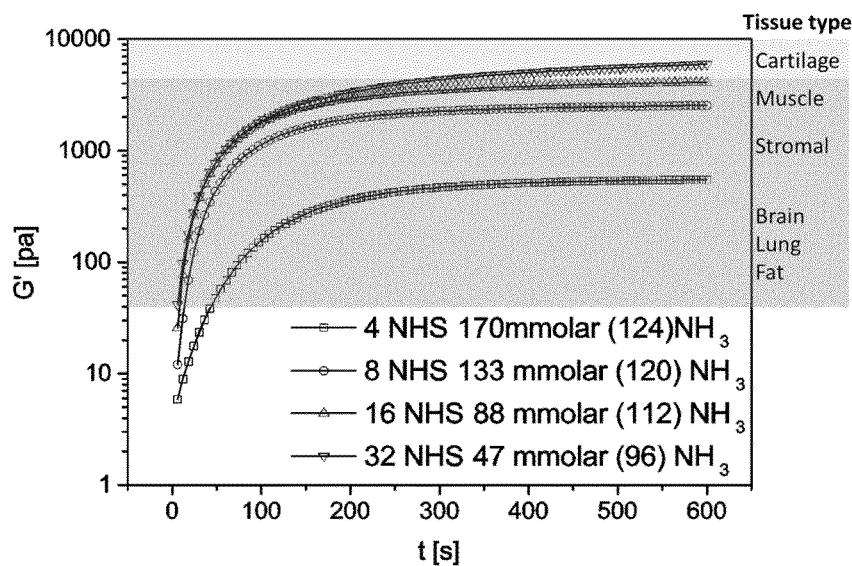
FIG. 5: Rheological evaluation in real-time during cross-linking. (a) G' plotted against time during cross-linking for 4, 8, 16 and 32 out of 128 possible cross-links.

Gels were made in situ the rheometer, equipped with a Peltier plate-plate accessory, using a stainless-steel upper geometry (0=20 mm) at a temperature of 34° C. The amine functional polymer was dissolved in water together with NaHCO$_3$ (amount eq. to a pH of 7.4 as determined by titration). The NHS cross-linker (4, 8, 16, 32 or 64 eq. per LD co-polymer) was dissolved in a separate vial in Milli-Q water. Both components were deposited separately in the rheometer (final composition 10 wt-% solid) and mixed with a pre shear program of 30 rad/s for 3 seconds. Time sweeps were conducted at strain (Y)=1% and frequency (ω)=1 Hz. To ensure all measurements were carried out in the linear viscoelastic region (LVR), complimentary frequency and amplitude sweeps were carried out from 0.01 to 100 rad/s and 0.01 to 100% strain. All measurements were performed in triplicates. Gels were successfully prepared with moduli ranging from 300-8000 pa, results are shown in FIG. 5.

MMC Antibacterial Effect of Gels.

Figure 7:
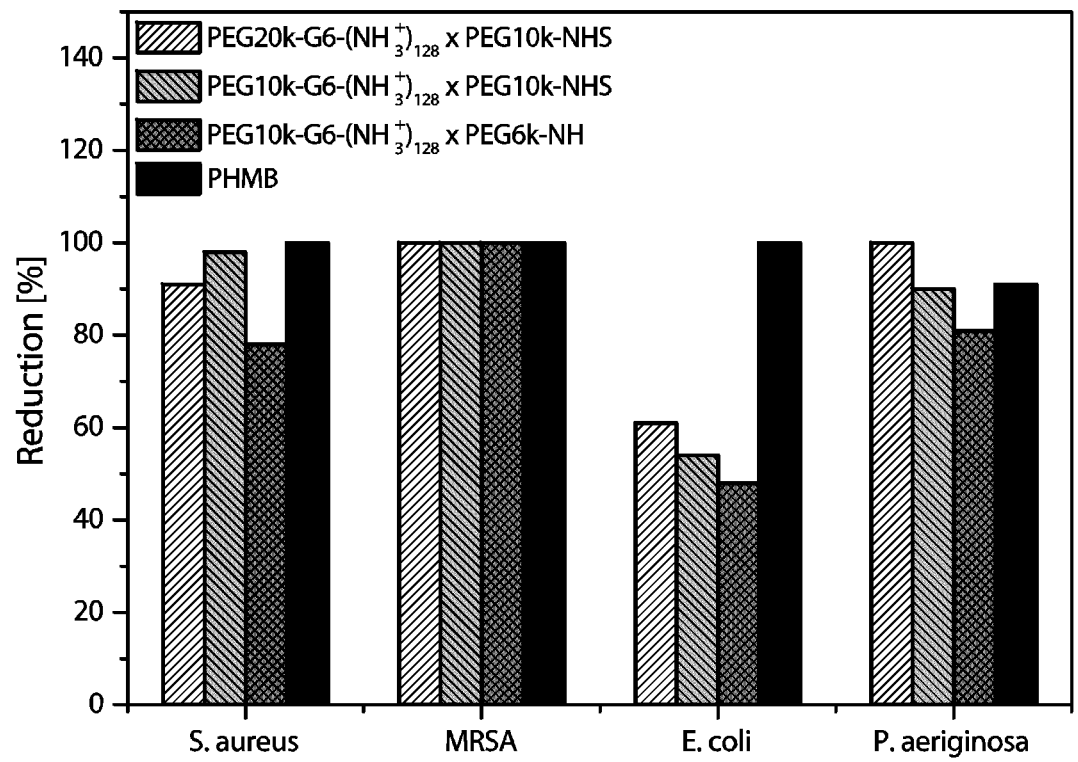
FIG. 7: MMC assay of gels comprising co-polymers PEG20k-G6-$(NH_3^+)_{128}$ and PEG10k-G6-$(NH_3^+)_{128}$ cross-linked with PEG10k-NHS and PEG20k-NHS, respectively on 24-wellplate blood agar varying the length of the linear segment of the active co-polymer as well as the length of the cross-linker. Both gram positive (*S. aureus* (SA) and Methicillin resistant resistant *S. aureus* (MRSA)) as well as gram negative (*E. coli* and *P. aeriginosa*) bacteria where tested.

Test/control substances are added on top of horse blood-agar in a 24-wellplate. Gels used in this study were PEG10k-G6-(NH$_3^+$)$_{128}$ cross-linked with PEG10k-NHS, PEG6K—NHS and PEG20k-G6-(NH$_3^+$)$_{128}$ cross-linked with PEG10k-NHS. Gels with a thickness of 400 μm where used together with a bacterial concentration of 100 CFU well$^{-1}$. After gelling or drying of the substances 40 μl of bacterial suspension, of 2.5×10$^3$ CFU mL$^{-1}$ corresponding to 100 CFU 40 μL$^{-1}$, is added to each well. The well plate is then incubated aerobically overnight for about 16 h at 37° C. The bacterial growth is quantified by counting CFU and the growth reduction compared to untreated control calculated. The gels where evaluated using four bacterial strains: *E. coli* CCUG 17620 (ATCC 25922, *S. aureus* CCUG 15915 (ATCC 29213), *Staphylococcus aureus* (MRSA) CCUG 31966, *Pseudomonas aeruginosa* CCUG 17619 (ATCC 27853). An antibacterial effect was observed for all tested gels. The highers effect was observed for PEG20k-G6-(NH$_3^+$)$_{128}$ cross-linked with PEG10k-NHS, results are shown in FIG. 7.

In Vivo Antimicrobial Evaluation

Figure 8:
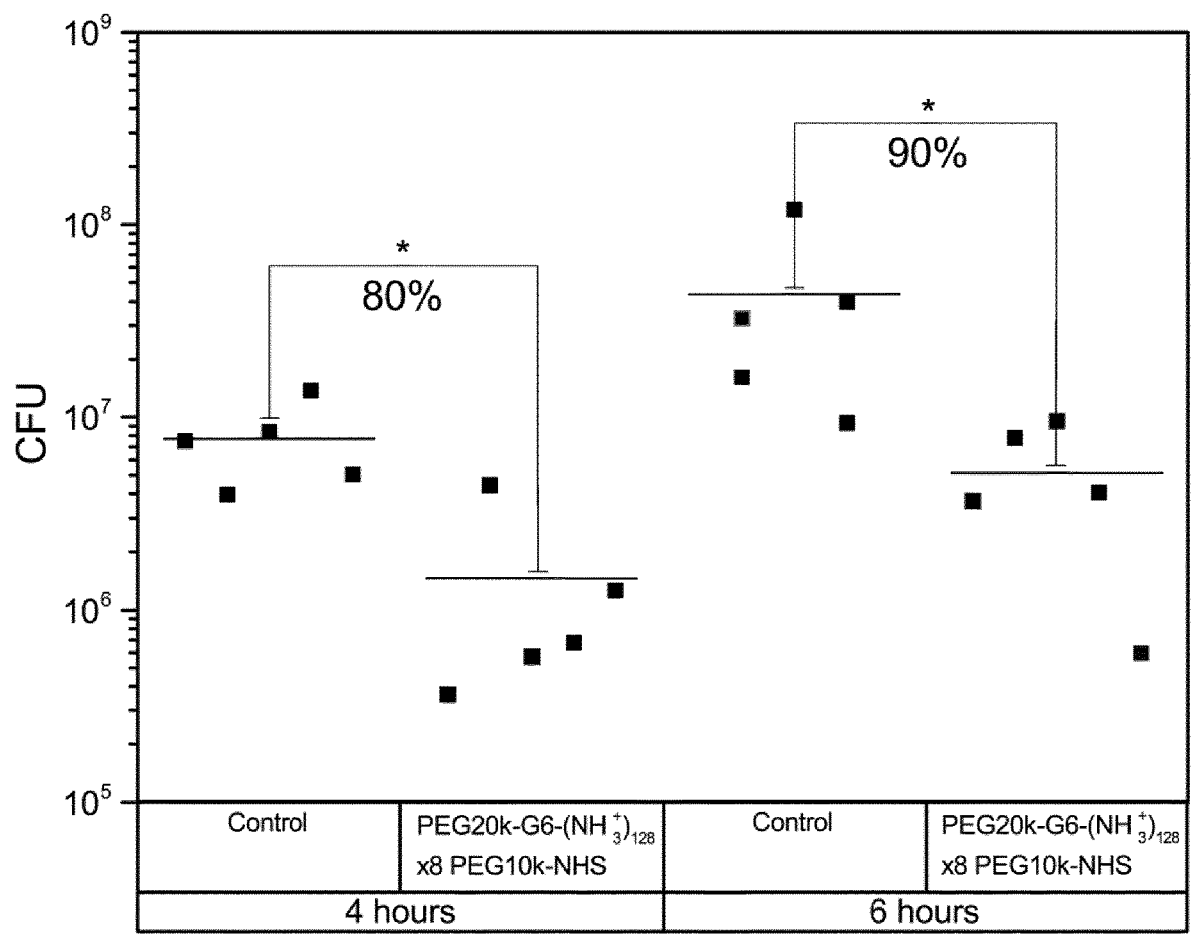
FIG. 8: In vivo test mouse model. The co-polymer (PEG20K-G6-β-Alanin) inhibited the bacterial growth by 80% 4 hour's post infection and 90% 6 hours post infection. Staples represents average and error bars SEM. Statistical method Mann-Whitney U-test. *=$p<0.05$. N=5 for each group.

The animal experiments in the present study were performed after prior approval from the local ethics committee for animal studies at the administrative court of appeals in Gothenburg, Sweden. The method is modiefied from R. J. Mcripley, R. R. Whitney, Antimicrob Agents Ch 1976, 10, 38 and J. Hakansson, C. Bjorn, K. Lindgren, E. Sjostrom, V. Sjostrand, M. Mahlapuua, Antimicrob Agents Ch 2014, 58, 2982.Eight mL of bacterial suspension (*Staphylococcus aureus* (ATCC 29213) 10$^9$ CFU mL$^{-1}$) were prepared and 3-0 silc sutures (684G, Ethicon) were soaked for 30 min in the suspension and then dried on filter paper at +4° C. for 30 min. The infected sutures were kept at +4° C. until used. Female mice of CD1 strain (25-30 g, Charles River, Sulzfeldt, Germany) were used. They had free access to water and pellets. There were five mice in each group for all experiments. The mice were anaesthetized with isoflurane, the back of the mouse was shaved with a clipper, washed with 70% ethanol and a 1 cm full-thickness incision wound was placed centrally on the back of the mouse in the neck region with a scalpel. The wound and surrounding skin tissue was covered with 100 μl of polymer (PEG20K-G6-beta-Alanin) using twin syringe biomaterial delivery system and the film was let to polymerize for 5 min One cm of the infected suture (corresponding to approximately 10$^6$ CFU) was placed into the wound. Two sutures (5-0 Ethilon*II (EH7800H, Ethicon, Sollentuna, Sweden) were attached over the incision. Buprenorfin (48 μg kg$^{-1}$, Temgesic) was given preoperatively by intraperitoneal injection, for post-surgical pain relief. The mice were euthanized 4 and 6 h post-infection and an area of 2 by 1 cm around the wound was excised and homogenized with a rotor stator homogenizer in 2 mL ice cold 0.037% BHI. The homogenate was centrifuged at 2000×g for 10 min at 4° C., the supernatant was discarded and the pellet in 2 mL phosphate buffer (0.05% Triton X-100 in 0.0375 M phosphate buffer). This suspension was diluted in five 10-fold steps by transferring 22.2 to 200 μL phosphate buffer in a 96-well plate. Fifty microliters of each dilution, including the original suspension, were transferred to horse blood agar plates and incubated at +37° C. overnight. The colonies on the plates containing 30-300 CFU were counted and the number of CFU per wound was determined. The data are presented as % of the control group (no treatment) and as CFU. An 80% reduction of bacteria after 4 hours and after 6 hours, a full log (90%) reduction in bacteria was observed, results are shown in FIG. 8.

The invention claimed is:

1. A method for the treatment of a bacterial infection, said method comprising administering to a subject in need thereof a pharmaceutically effective amount of a co-polymer selected from the group consisting of PEG10K-(G4-β-Alanin), PEG10K-(G5-β-Alanin), PEG10K-(G6-β-Alanin), PEG20K-(G4-β-Alanin), PEG20K-(G5-β-Alanin), PEG20K-(G6-β-Alanin), PEG2K-(G4-β-Alanin), PEG2K-(G5-β-Alanin), PEG2K-(G6-β-Alanin), PEG5K-(G4-β-Alanin), PEG5K-(G5-β-Alanin) and PEG5K-(G6-β-Alanin), a hyperbranched variant thereof, or any combination thereof.

2. The method of claim 1, wherein said co-polymer is present in a composition further comprising a cross-linking agent, wherein said composition comprises more than one type of the co-polymer.

3. The method of claim 1, wherein said cross-linking agent comprises or is polyethylene glycol (PEG) having a molecular weight of 0.5 to 50 kDa or 1 to 50 kDa.

4. The method of claim 3, wherein said cross-linking agent comprises PEG10K-COO-N-hydroxysuccinimide (NHS).

5. The method of claim 4, wherein the molar ratio between the crosslinking functional groups on the cross-linking agent and the carboxylic amines of the co-polymer are in the range of 1:4 to 1:64.

6. The method of claim 1, wherein the bacterial infection is caused by a gram negative or a gram positive bacteria selected from the group consisting of *Staphylococcus aureus, Pseudomonas aeruginosa, Escherichia coli, Staphylococcus epidermidis*, and *Propionibacterium acnes* and *Enterococcus faecalis*.

7. The method of claim 4, wherein said composition is coated onto a wound dressing to be applied or attached onto a body tissue or wound surface.

8. The method of claim 7, wherein said composition is in the form of a biodegradable hydrogel.

9. A co-polymer comprising a water soluble backbone polymer having in at least one end a dendritic or hyperbranched polymer, wherein said dendritic or hyperbranched polymer is of generation 6 (G6) and wherein at least one functional group comprising a carboxylic amine is covalently attached to the periphery of the dendritic or hyperbranched polymer, wherein said co-polymer is selected from the group consisting of PEG20k-G6-$(NH_3^+)_{128}$, PEG10k-G6-$(NH_3^+)_{128}$, PEG5k-G6-$(NH_3^+)_{128}$, and PEG2k-G6-$(NH_3^+)_{128}$.

10. The co-polymer of claim 9, wherein said co-polymer is selected from the group consisting of PEG10K-(G6-β-Alanin) and PEG20K-(G6-β-Alanin), PEG5K-(G6-β-Alanin) and PEG2K-(G6-β-Alanin), or a hyperbranched variant thereof.

11. A biodegradable hydrogel comprising a co-polymer of claim 9, said hydrogel further comprising a cross-linking agent.

12. A kit of parts comprising:
a) a dispenser comprising a co-polymer or a composition comprising a co-polymer, wherein said co-polymer is selected from the group consisting of PEG10K-(G4-β-Alanin), PEG10K-(G5-β-Alanin), PEG10K-(G6-β-Alanin), PEG20K-(G4-β-Alanin), PEG20K-(G5-β-Alanin), PEG20K-(G6-β-Alanin), PEG2K-(G4-β-Alanin), PEG2K-(G5-β-Alanin), PEG2K-(G6-β-Alanin), PEG5K-(G4-β-Alanin), PEG5K-(G5-β-Alanin) and PEG5K-(G6-β-Alanin), a hyperbranched variant thereof, or any combination thereof, and
b) a dispenser comprising a cross-linking agent, said cross-linking agent comprising polyethylene glycol (PEG) having a molecular weight of 0.5 to 50 kDa.

13. A method for coating a surface of a human or animal body, or a surface of a medical implant, with a composition comprising a cross-linked co-polymer, said method comprising the steps of:
a) mixing a solution comprising a co-polymer, wherein said co-polymer is selected from the group consisting of PEG10K-(G4-β-Alanin), PEG10K-(G5-β-Alanin), PEG10K-(G6-β-Alanin), PEG20K-(G4-β-Alanin), PEG20K-(G5-β-Alanin), PEG20K-(G6-β-Alanin), PEG2K-(G4-β-Alanin), PEG2K-(G5-β-Alanin), PEG2K-(G6-β-Alanin), PEG5K-(G4-β-Alanin), PEG5K-(G5-β-Alanin) and PEG5K-(G6-β-Alanin), a hyperbranched variant thereof, or any combination thereof, with a cross-linking agent, said cross-linking agent comprising polyethylene glycol (PEG) having a molecular weight of 0.5 to 50 kDa to yield a hydrogel comprising a cross-linked co-polymer, and thereafter;
b) applying a coating of said hydrogel comprising said cross-linked co-polymer onto said surface, wherein said mixing is performed no more than about 10 minutes before the hydrogel is to be applied to said surface and wherein said coating has as a thickness of no less than 50 μm and up to about 400 μm.

* * * * *